(12) United States Patent
Foerster et al.

(10) Patent No.: US 9,357,993 B2
(45) Date of Patent: Jun. 7, 2016

(54) KNOTLESS SUTURE ANCHORING DEVICE HAVING DEFORMING SECTION TO ACCOMMODATE SUTURES OF VARIOUS DIAMETERS

(71) Applicant: ArthroCare Corporation, Austin, TX (US)

(72) Inventors: Seth A. Foerster, San Clemente, CA (US); Francis Vijay, Irvine, CA (US); Jean Woloszko, Austin, TX (US)

(73) Assignee: ArthroCare Corporation, Austin, TX (US)

( * ) Notice: Subject to any disclaimer, the term of this patent is extended or adjusted under 35 U.S.C. 154(b) by 235 days.

(21) Appl. No.: 14/150,970

(22) Filed: Jan. 9, 2014

(65) Prior Publication Data

US 2014/0207189 A1 Jul. 24, 2014

Related U.S. Application Data

(63) Continuation of application No. 11/916,135, filed as application No. PCT/US2006/021125 on Jun. 1, 2006, now Pat. No. 8,657,854, which is a continuation-in-part of application No. 11/143,132, filed on Jun. 1, 2005, now abandoned, which is a continuation-in-part of application No. 09/781,793, filed on Feb. 12, 2001, now Pat. No. 7,083,638.

(60) Provisional application No. 60/799,116, filed on May 8, 2006.

(30) Foreign Application Priority Data

Jun. 1, 2006 (WO) ................. PCT/US2006/021125

(51) Int. Cl.
*A61B 17/04* (2006.01)
*A61F 2/08* (2006.01)

(52) U.S. Cl.
CPC ........... *A61B 17/0401* (2013.01); *A61F 2/0811* (2013.01); *A61B 17/0487* (2013.01); *A61B 2017/045* (2013.01); *A61B 2017/0409* (2013.01); *A61B 2017/0414* (2013.01); *A61B 2017/0417* (2013.01); *A61B 2017/0458* (2013.01); *A61B 2017/0496* (2013.01); *A61F 2/0805* (2013.01); *A61F 2002/0835* (2013.01); *A61F 2002/0864* (2013.01); *A61F 2002/0882* (2013.01); *A61F 2002/0888* (2013.01)

(58) Field of Classification Search
CPC ........... A61B 17/0401; A61B 17/0487; A61B 2017/0409; A61B 2017/0414; A61B 2017/0417; A61B 2017/045; A61B 2017/0458; A61B 2017/0496; A61F 2002/0835
See application file for complete search history.

(56) References Cited

U.S. PATENT DOCUMENTS 8,657,854 B2 * 2/2014 Foerster et al. ............... 606/232

*Primary Examiner* — Gregory Anderson
(74) *Attorney, Agent, or Firm* — Norman F. Hainer, Jr.

(57) ABSTRACT

An innovative bone anchor and methods for securing soft tissue, such as tendons, to bone, which permit a suture attachment that lies entirely beneath the cortical bone surface. The suturing material between the soft tissue and the bone anchor may be secured without the need for tying a knot. The suture attachment to the bone anchor involves the looping of a length of suture around a suture return member or path within the bone anchor, tightening the suture and attached soft tissue, and compressing the suture against the bone anchor. The bone anchor may be a tubular body having a lumen with a locking plug that compresses the suture therein. One of the components of the locking structure may include a deformable or flexible section, member, or surface. The locking plug may include a shaft and an enlarged head that interferes with the tubular body to provide a positive stop. An actuation rod attached at a frangible section to the shaft may be manipulated by an external handle during locking of the suture within the bone anchor. The bone anchor further may include locking structure for securing itself within a bone cavity.

20 Claims, 16 Drawing Sheets

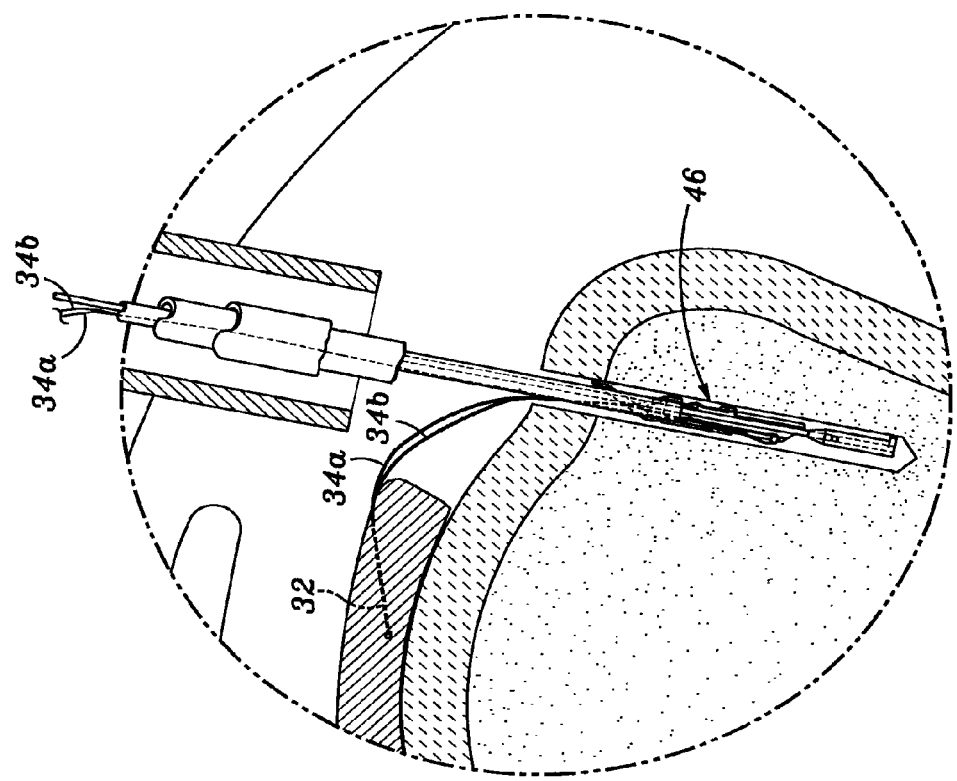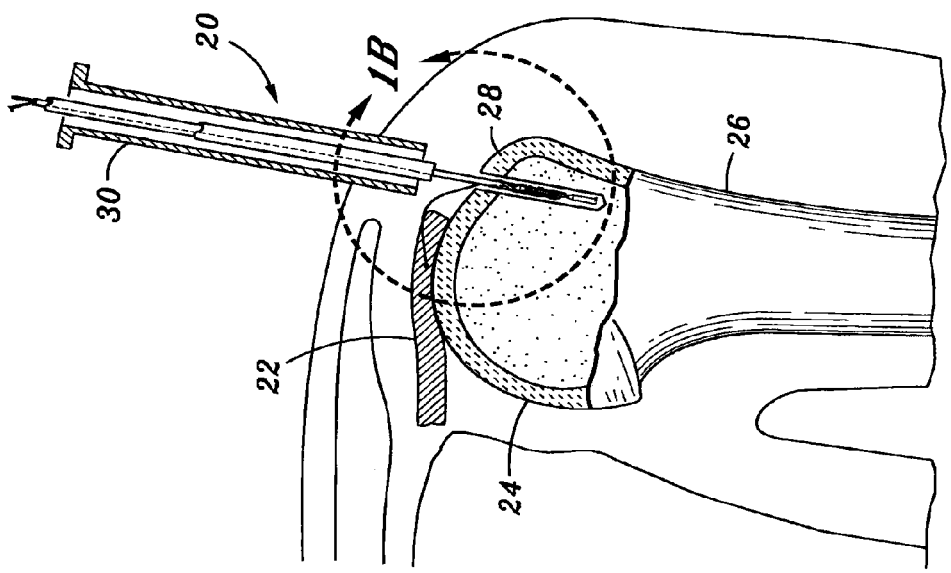
Fig. 1B
Fig. 1A

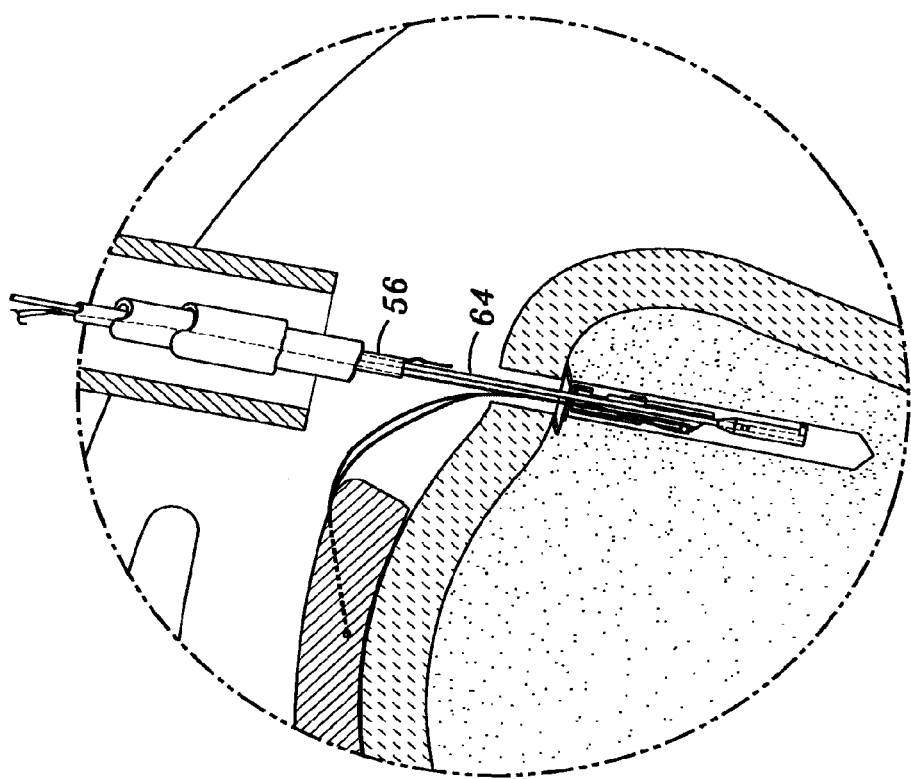
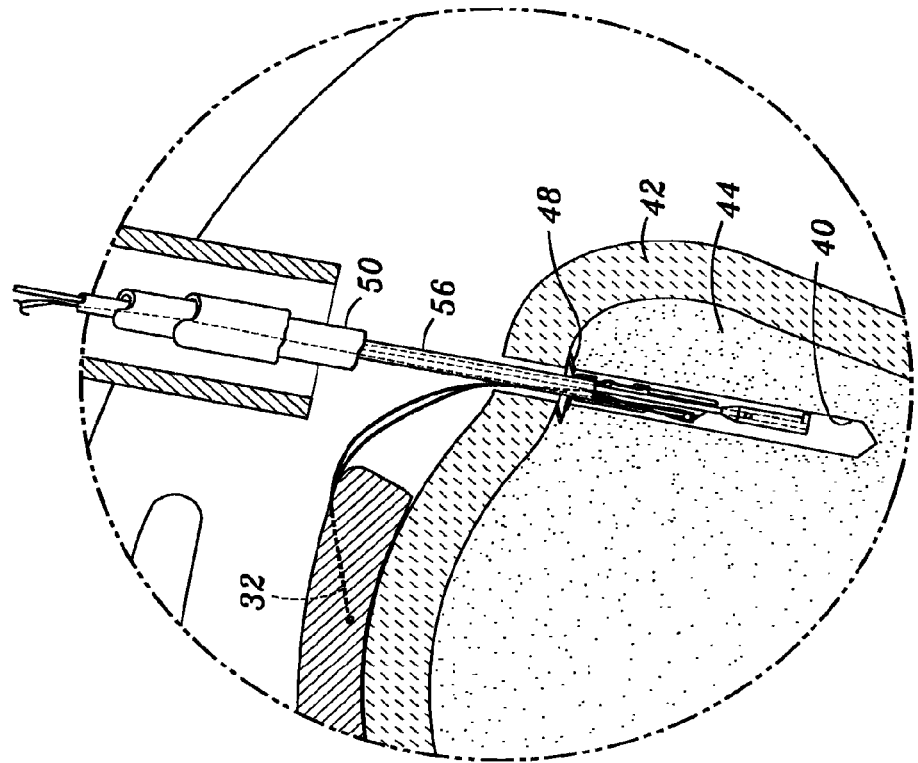

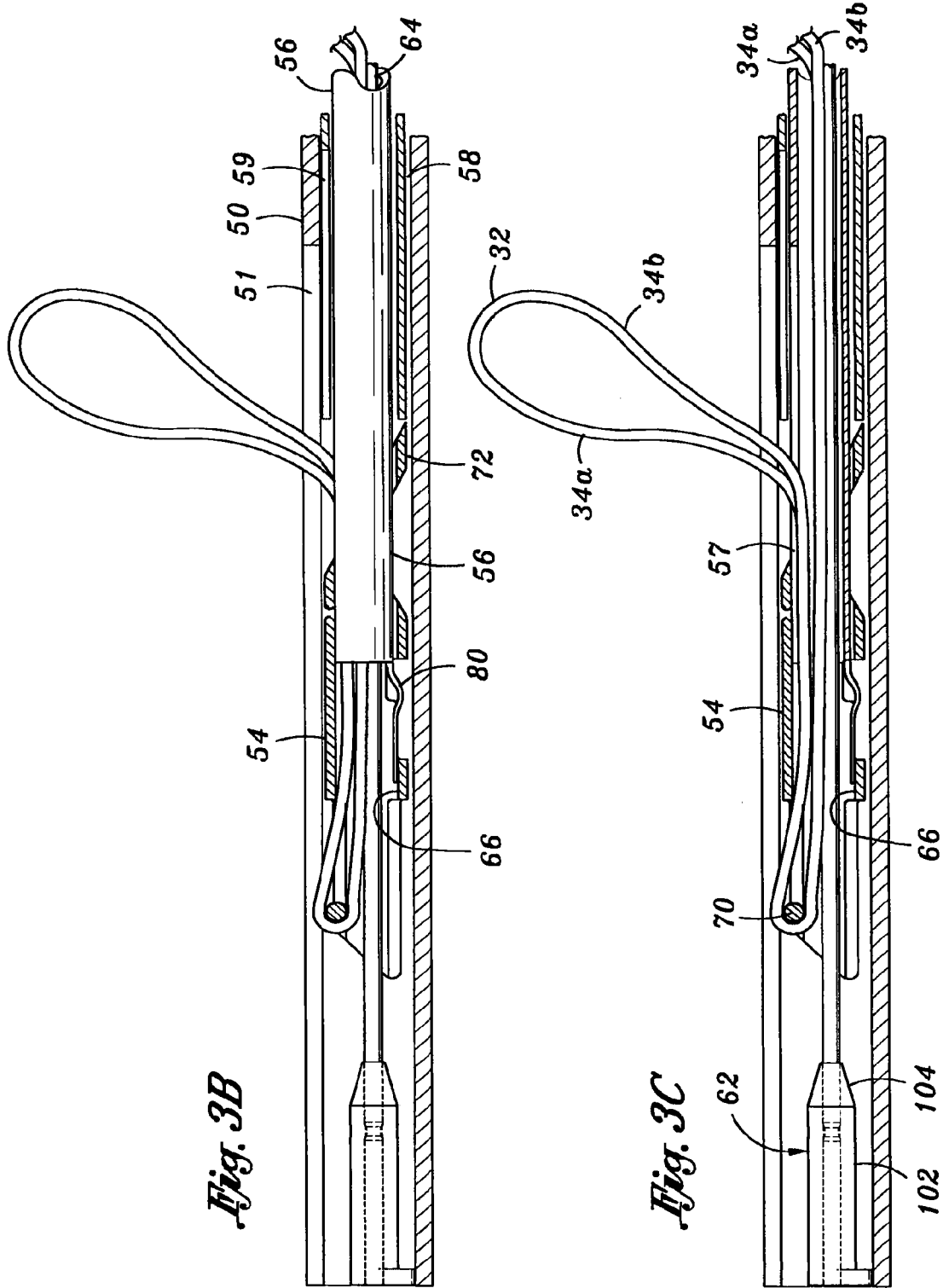

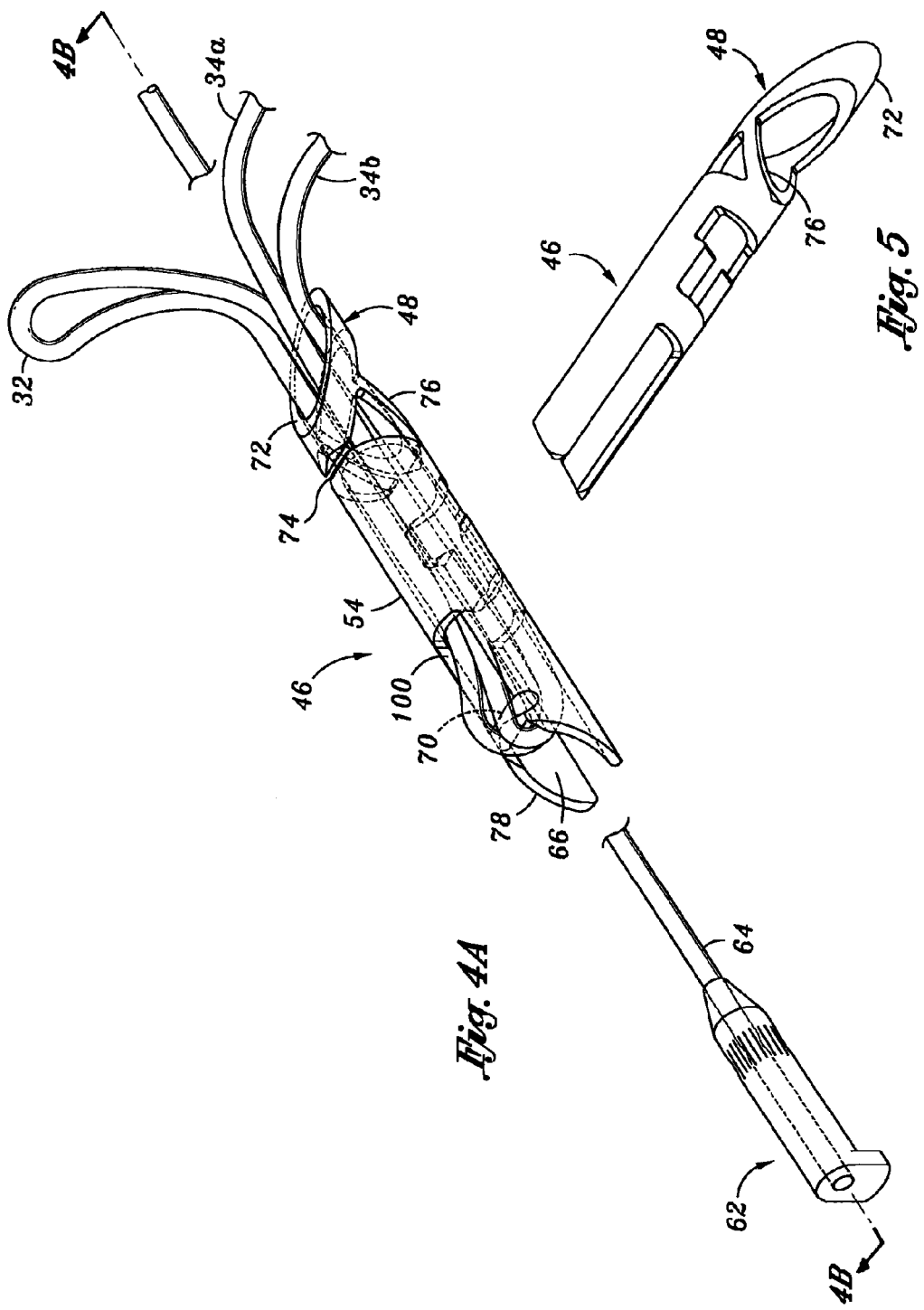

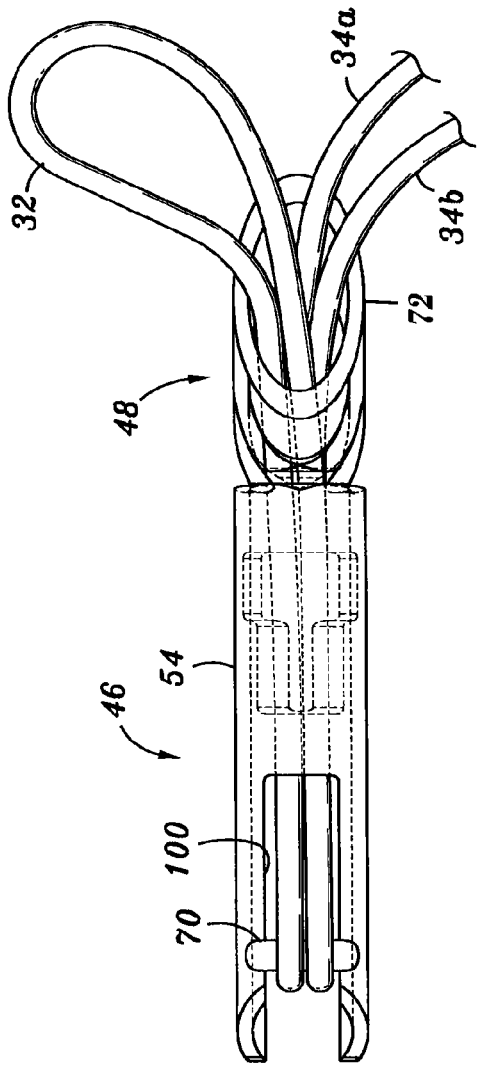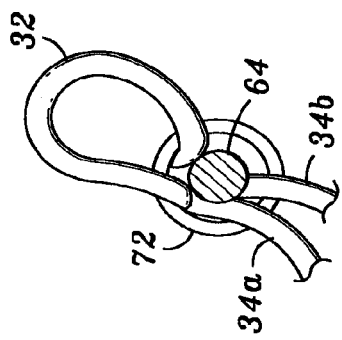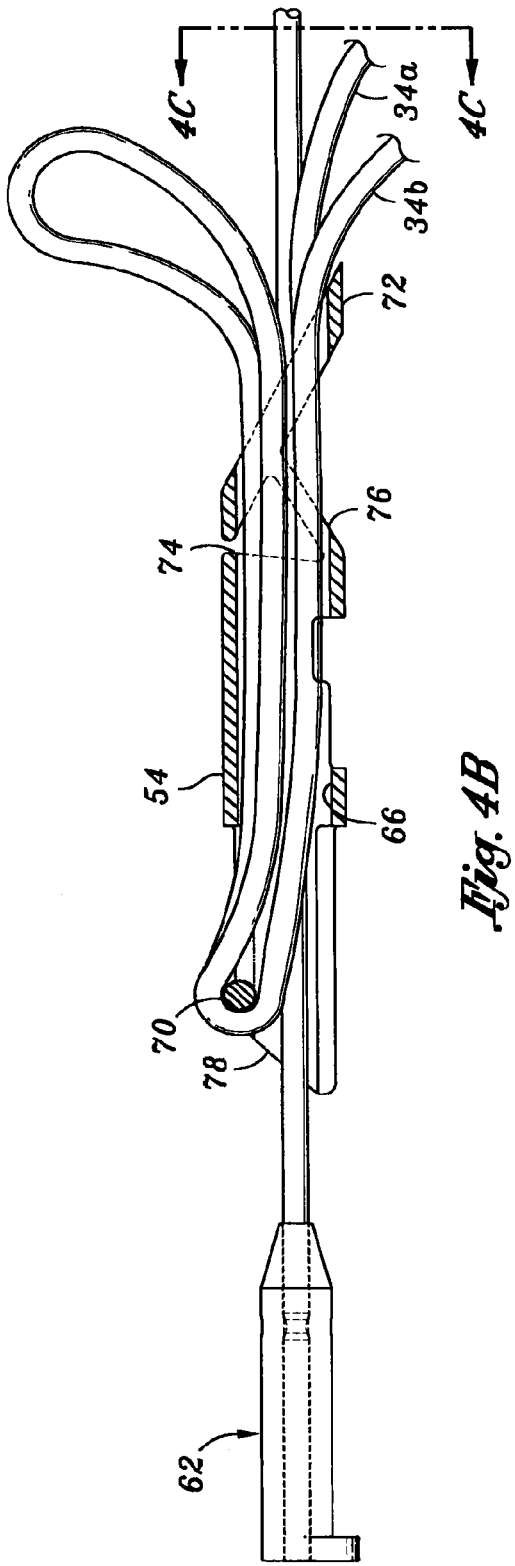

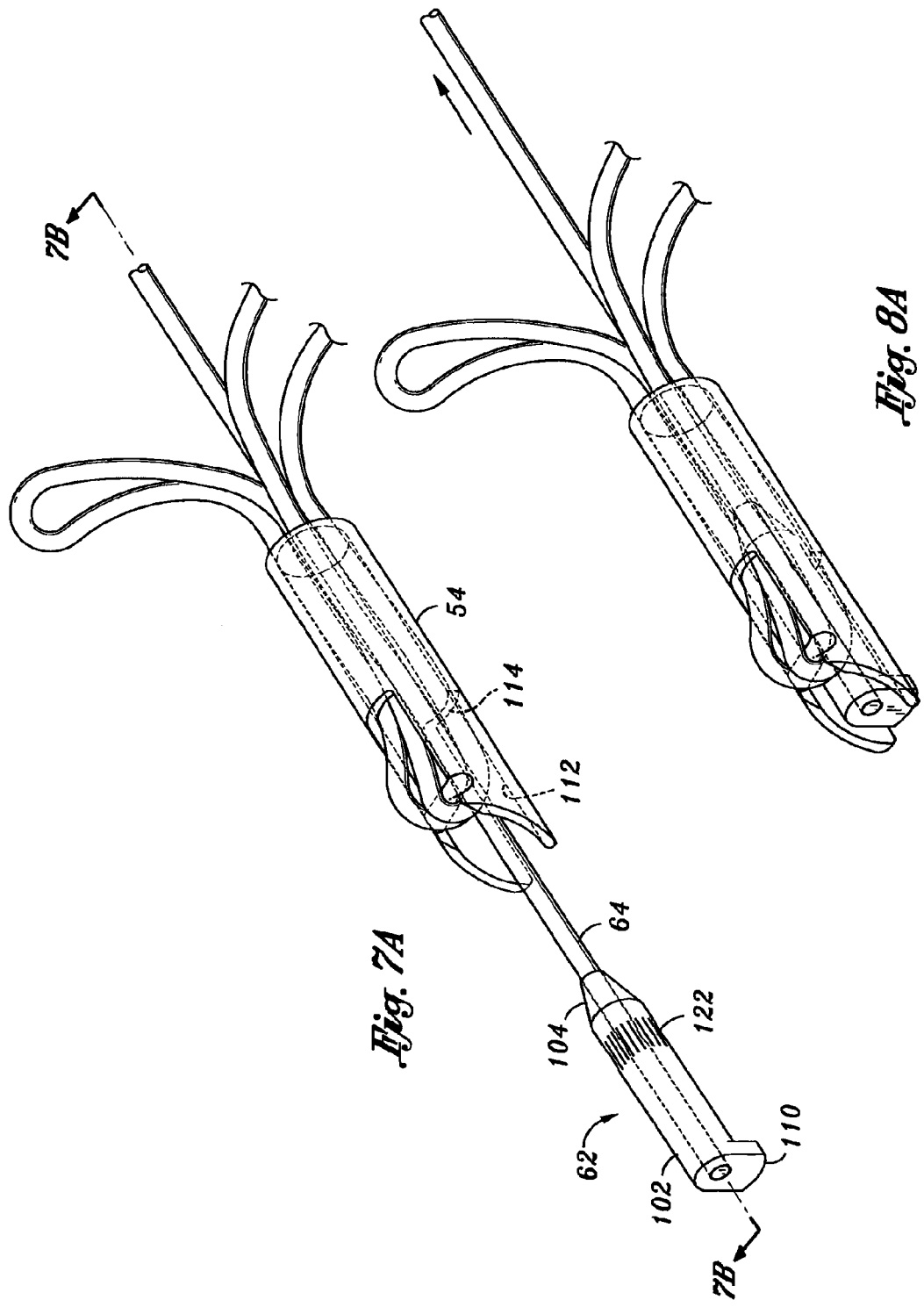

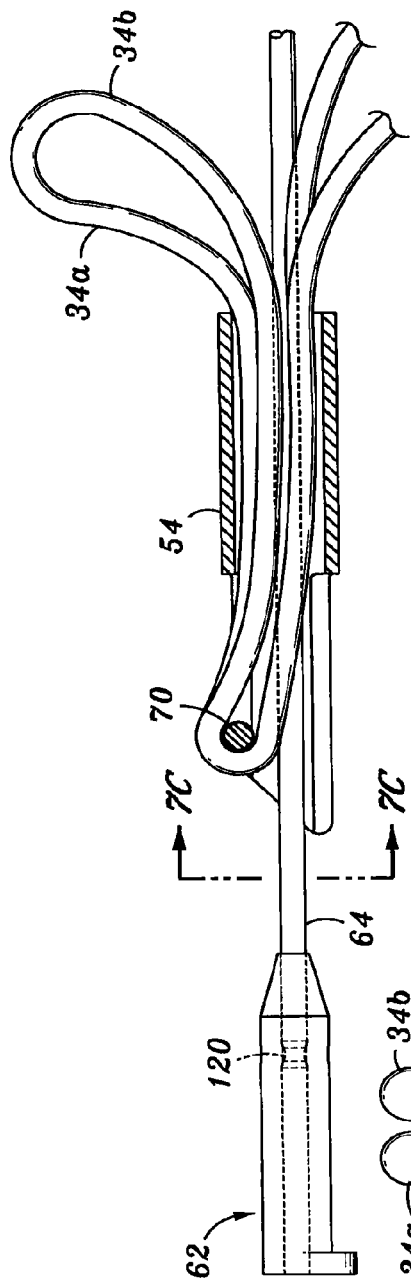
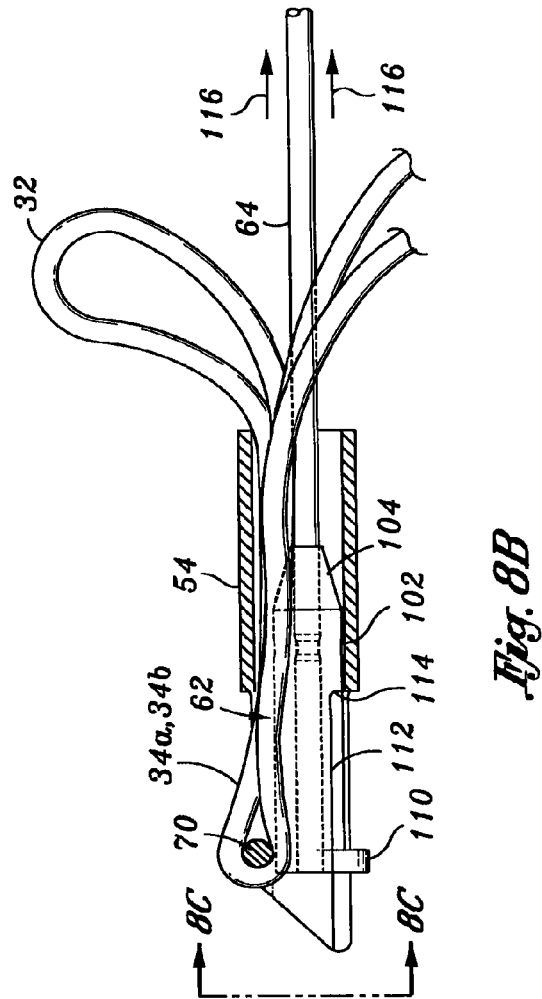
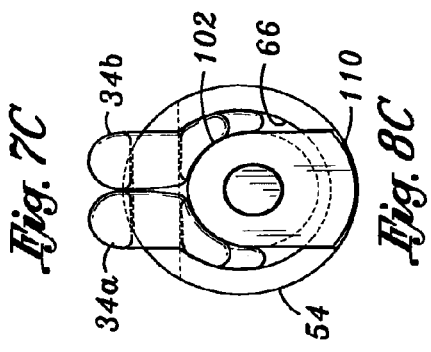

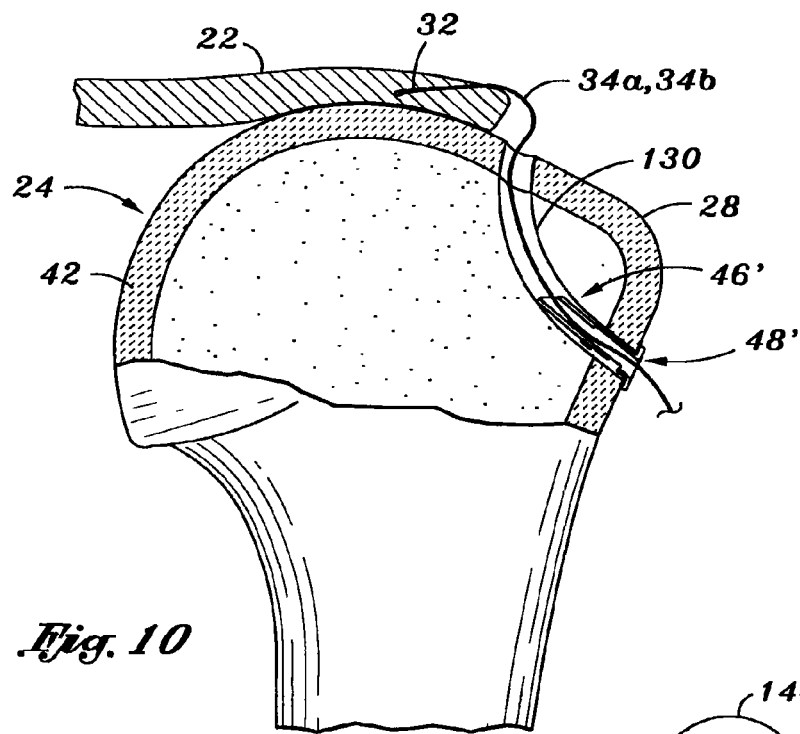
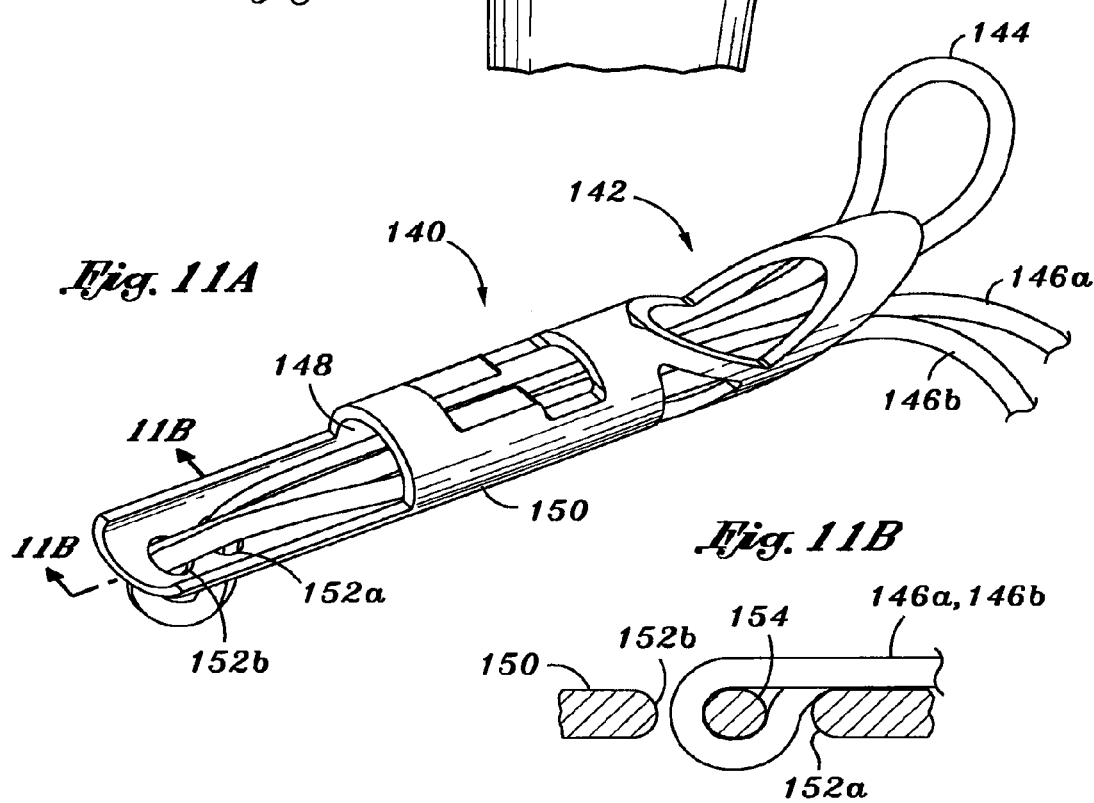

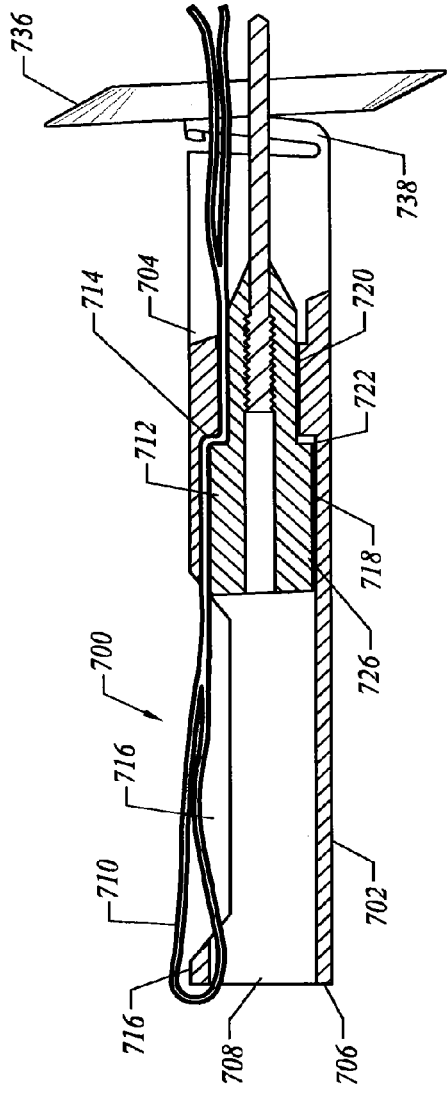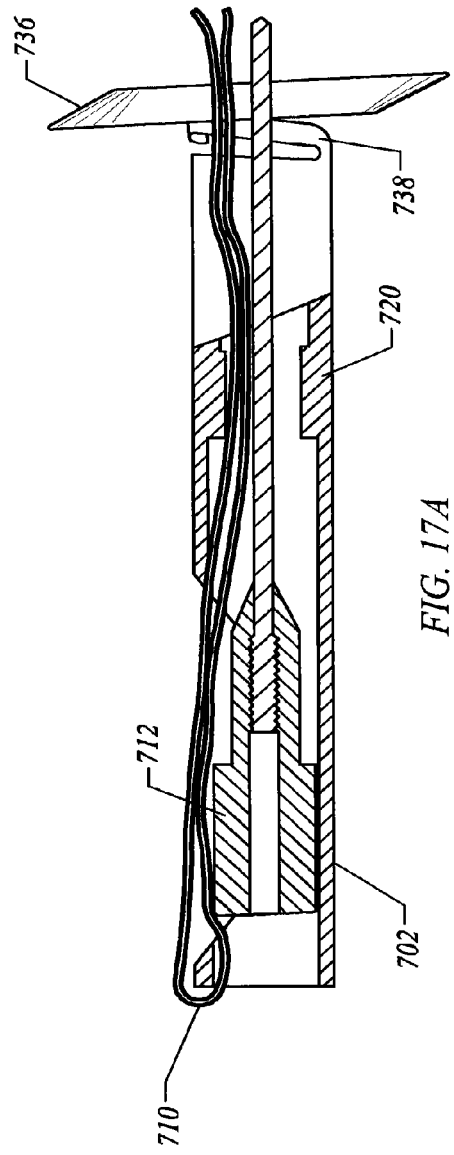
FIG. 17B
FIG. 17A

KNOTLESS SUTURE ANCHORING DEVICE HAVING DEFORMING SECTION TO ACCOMMODATE SUTURES OF VARIOUS DIAMETERS

CROSS-REFERENCE TO RELATED APPLICATIONS

This application is a continuation of application Ser. No. 11/916,135 filed May 28, 2008, which is the U.S. National Stage of International Patent Application No. PCT/US2006/021125 filed Jun. 1, 2006, which claims the benefit of U.S. Provisional Application No. 60/799,116 filed May 8, 2006. PCT/US2006/021125 is a continuation-in-part of U.S. patent application Ser. No. 11/143,132 filed Jun. 1, 2005, which is a continuation-in-part of Ser. No. 09/781,793 filed Feb. 12, 2001, now U.S. Pat. No. 7,083,638.

BACKGROUND OF THE INVENTION

This invention relates generally to methods and apparatus for attaching soft tissue to bone, and more particularly to anchors and methods for securing connective tissue, such as ligaments or tendons, to bone. The invention has particular application to arthroscopic surgical techniques for reattaching the rotator cuff to the humeral head, in order to repair the rotator cuff.

It is an increasingly common problem for tendons and other soft, connective tissues to tear or to detach from associated bone. One such type of tear or detachment is a "rotator cuff" tear, wherein the supraspinatus tendon separates from the humerus, causing pain and loss of ability to elevate and externally rotate the arm. Complete separation can occur if the shoulder is subjected to gross trauma, but typically, the tear begins as a small lesion, especially in older patients.

To repair a torn rotator cuff, the typical course today is to do so surgically, through a large incision. This approach is presently taken in almost 99% of rotator cuff repair cases. There are two types of open surgical approaches for repair of the rotator cuff, one known as the "classic open" and the other as the "mini-open". The classic open approach requires a large incision and complete detachment of the deltoid muscle from the acromion to facilitate exposure. The cuff is debrided to ensure suture attachment to viable tissue and to create a reasonable edge approximation. In addition, the humeral head is abraded or notched at the proposed soft tissue to bone reattachment point, as healing is enhanced on a raw bone surface. A series of small diameter holes, referred to as "transosseous tunnels", are "punched" through the bone laterally from the abraded or notched surface to a point on the outside surface of the greater tuberosity, commonly a distance of 2 to 3 cm. Finally, the cuff is sutured and secured to the bone by pulling the suture ends through the transosseous tunnels and tying them together using the bone between two successive tunnels as a bridge, after which the deltoid muscle must be surgically reattached to the acromion. Because of this maneuver, the deltoid requires postoperative protection, thus retarding rehabilitation and possibly resulting in residual weakness. Complete rehabilitation takes approximately 9 to 12 months.

The mini-open technique, which represents the current growing trend and the majority of all surgical repair procedures, differs from the classic approach by gaining access through a smaller incision and splitting rather than detaching the deltoid. Additionally, this procedure is typically performed in conjunction with arthroscopic acromial decompression. Once the deltoid is split, it is retracted to expose the rotator cuff tear. As before, the cuff is debrided, the humeral head is abraded, and the so-called "transosseous tunnels", are "punched" through the bone or suture anchors are inserted. Following the suturing of the rotator cuff to the humeral head, the split deltoid is surgically repaired.

Although the above described surgical techniques are the current standard of care for rotator cuff repair, they are associated with a great deal of patient discomfort and a lengthy recovery time, ranging from at least four months to one year or more. It is the above described manipulation of the deltoid muscle together with the large skin incision that causes the majority of patient discomfort and an increased recovery time.

Less invasive arthroscopic techniques are beginning to be developed in an effort to address the shortcomings of open surgical repair. Working through small trocar portals that minimize disruption of the deltoid muscle, a few surgeons have been able to reattach the rotator cuff using various bone anchor and suture configurations. The rotator cuff is sutured intracorporeally and an anchor is driven into bone at a location appropriate for repair. Rather than thread the suture through transosseous tunnels which are difficult or impossible to create arthroscopically using current techniques, the repair is completed by tying the cuff down against bone using the anchor and suture. Early results of less invasive techniques are encouraging, with a substantial reduction in both patient recovery time and discomfort.

Unfortunately, the skill level required to facilitate an entirely arthroscopic repair of the rotator cuff is inordinately high. Intracorporeal suturing is clumsy and time consuming, and only the simplest stitch patterns can be utilized. Extracorporeal knot tying is somewhat less difficult, but the tightness of the knots is difficult to judge, and the tension cannot later be adjusted. Also, because of the use of bone anchors to provide a suture fixation point in the bone, the knots that secure the soft tissues to the anchor by necessity leave the knot bundle on top of the soft tissues. In the case of rotator cuff repair, this means that the knot bundle is left in the shoulder capsule where it can be felt by the patient postoperatively when the patient exercises the shoulder joint. So, knots tied arthroscopically are difficult to achieve, impossible to adjust, and are located in less than optimal areas of the shoulder. Suture tension is also impossible to measure and adjust once the knot has been fixed. Consequently, because of the technical difficulty of the procedure, presently less than 1% of all rotator cuff procedures is of the arthroscopic type, and is considered investigational in nature.

Another significant difficulty with current arthroscopic rotator cuff repair techniques is shortcomings related to currently available suture anchors. Suture eyelets in bone anchors available today, which like the eye of a needle are threaded with the thread or suture, are small in radius, and can cause the suture to fail at the eyelet when the anchor is placed under high tensile loads.

There are various bone anchor designs available for use by an orthopedic surgeon for attachment of soft tissues to bone. The basic commonality between the designs is that they create an attachment point in the bone for a suture that may then be passed through the soft tissues and tied, thereby immobilizing the soft tissue. This attachment point may be accomplished by different means. Screws are known for creating such attachments, but suffer from a number of disadvantages, including their tendency to loosen over time, requiring a second procedure to later remove them, and their requirement for a relatively flat attachment geometry.

Another approach is to utilize the difference in density in the cortical bone (the tough, dense outer layer of bone) and the cancellous bone (the less dense, airy and somewhat vascular interior of the bone). There is a clear demarcation between the cortical bone and cancellous bone, where the cortical bone presents a kind of hard shell over the less dense cancellous bone. The aspect ratio of the anchor is such that it typically has a longer axis and a shorter axis and usually is pre-threaded with a suture. These designs use a hole in the cortical bone through which an anchor is inserted. The hole is drilled such that the shorter axis of the anchor will fit through the diameter of the hole, with the longer axis of the anchor being parallel to the axis of the drilled hole. After deployment in to the cancellous bone, the anchor is rotated 90° so that the long axis is aligned perpendicularly to the axis of the hole. The suture is pulled, and the anchor is seated up against the inside surface of the cortical layer of bone. Due to the mismatch in the dimensions of the long axis of the anchor and the hole diameter, the anchor cannot be retracted proximally from the hole, thus providing resistance to pull-out. These anchors still suffer from the aforementioned problem of eyelet design that stresses the sutures.

Still other prior art approaches have attempted to use a "pop rivet" approach. This type of design requires a hole in the cortical bone into which a split shaft is inserted. The split shaft is hollow, and has a tapered plug leading into its inner lumen. The tapered plug is extended out through the top of the shaft, and when the plug is retracted into the inner lumen, the tapered portion causes the split shaft to be flared outwardly, ostensibly locking the device into the bone.

Other methods of securing soft tissue to bone are known in the prior art, but are not presently considered to be feasible for shoulder repair procedures, because of physicians' reluctance to leave anything but a suture in the capsule area of the shoulder. The reason for this is that staples, tacks, and the like could possibly fall out and cause injury during movement. As a result of this constraint, the attachment point often must be located at a less than ideal position. Also, the tacks or staples require a substantial hole in the soft tissue, and make it difficult for the surgeon to precisely locate the soft tissue relative to the bone.

As previously discussed, any of the anchor points for sutures mentioned above require that a length of suture be passed through an eyelet fashioned in the anchor and then looped through the soft tissues and tied down to complete the securement. Much skill is required, however, to both place the sutures in the soft tissues, and to tie knots while working through a trocar under endoscopic visualization.

There have been attempts to solve some of the problems that exist in current anchor designs. One such approach is disclosed in U.S. Pat. No. 5,324,308 to Pierce. In this patent, there is disclosed a suture anchor that incorporates a proximal and distal wedge component having inclined mating faces. The distal wedge component has two suture thread holes at its base through which a length of suture may be threaded. The assembly may be placed in a drilled hole in the bone, and when tension is placed on the suture, the distal wedge block is caused to ride up against the proximal wedge block, expanding the projected area within the drilled hole, and locking the anchor into the bone. This approach is a useful method for creating an anchor point for the suture, but does not in any way address the problem of tying knots in the suture to fix the soft tissue to the bone.

The problem of placing sutures in soft tissues and tying knots in an endoscopic environment is well known, and there have been attempts to address the problem and to simplify the process of suture fixation. One such approach is disclosed in U.S. Pat. No. 5,383,905 to Golds et al. The patent describes a device for securing a suture loop about bodily tissue that includes a bead member having a longitudinal bore and an anchor member adapted to be slidably inserted within the bore of the bead member. The anchor member includes at least two axial compressible sections which define a passageway to receive two end portions of a suture loop. The axial sections collapse radially inwardly upon insertion of the anchor member within the bore of the bead member to securely wedge the suture end portions received within the passageway.

Although the Golds et al. patent approach utilizes a wedge-shaped member to lock the sutures in place, the suture legs are passing through the bore of the bead only one time, in a proximal to distal direction, and are locked by the collapsing of the wedge, which creates an interference on the longitudinal bore of the anchor member. Also, no provision is made in this design for attachment of sutures to bone. The design is primarily suited for locking a suture loop, such as is used for ligation or approximation of soft tissues.

An approach that includes bone attachment is described in U.S. Pat. No. 5,584,835 to Greenfield. In this patent, a two part device for attaching soft tissue to bone is shown. A bone anchor portion is screwed into a hole in the bone, and is disposed to accept a plug that has been adapted to receive sutures. In one embodiment, the suture plug is configured so that when it is forced into its receptacle in the bone anchor portion, sutures that have been passed through an eyelet in the plug are trapped by friction between the wall of the anchor portion and the body of the plug portion.

Although there is some merit to this approach for eliminating the need for knots in the attachment of sutures to bone, a problem with being able to properly set the tension in the sutures exists. The user is required to pull on the sutures until appropriate tension is achieved, and then to set the plug portion into the bone anchor portion. This action increases the tension in the sutures, and may garrot the soft tissues or increase the tension in the sutures beyond the tensile strength of the material, breaking the sutures. In addition, the minimal surface area provided by this anchor design for pinching or locking the sutures in place will abrade or damage the suture such that the suture's ability to resist load will be greatly compromised.

A disclosure that incorporates bone attachment and eliminates knot tying is set forth in U.S. Pat. No. 5,702,397 to Goble et al. One embodiment, in particular, is shown in FIG. 23 of that patent and includes a bone anchor that has a threaded body with an inner cavity. The cavity is open to one end of the threaded body, and joins two lumens that run out to the other end of the threaded body. Within the cavity is disposed a gear, journaled on an axle. A length of suture is threaded through one lumen, around the gear, and out through the other lumen. A ball is disposed within the cavity to ride against a tapered race and ostensibly lock the suture in place. What is not clear from the patent disclosure is how the force D shown as the tension in the suture would lock the ball into the race. Although this embodiment purports to be a self-locking anchor adapted for use in blind holes for fixing sutures into bone, the construct shown is complicated, and does not appear to be adequate to reliably fixate the suture.

What is needed, therefore, is a new approach for repairing the rotator cuff or fixing other soft tissues to bone, wherein suture tension can be adjusted and possibly measured, the suture anchor resides completely below the cortical bone surface, there is no requirement for the surgeon to tie a knot to attach the suture to the bone anchor, and wherein the procedure associated with the new approach is better for the patient, saves time, is uncomplicated to use, and easily taught to practitioners having skill in the art.

DISCLOSURE OF INVENTION

In accordance with one aspect of the present invention, a knotless suture anchor apparatus for anchoring a length of suture with respect to a body cavity comprises an anchor body having an anchoring structure for fixing the anchor body within a body cavity, and a suture locking plug. The anchor body has proximal and distal ends, and a lumen opening at the proximal end. A suture return member (such as a pulley) fixed with respect to the anchor body is provided such that a length of suture may be introduced into the lumen from the proximal end, looped around it, and passed out of lumen through the proximal end. The suture locking plug is movable within the lumen from a first position to a second position. The suture locking plug and lumen cooperate such that the suture locking plug does not interfere with axial movement of the length of suture in the first position and interferes with axial movement of the length of suture in the second position, preferably by compressing the length of suture against the anchor body.

In one aspect of the present invention, at least one of the anchor body, and the plug includes a flexing section, or member, that serves to accommodate and secure sutures having different diameters. In another aspect, an intermediate deforming member, or coating is present between the anchor body and the plug to provide additional conformity and to prevent axial movement of the suture without causing damage to the suture.

In a preferred embodiment, the anchor body is generally tubular and the lumen opens at the distal end as well as at the proximal end. The distal end of the anchor body may be discontinuous at one side thereof wherein a slot extends in a proximal direction from the discontinuity to a slot end. The suture locking plug includes a proximal section that fits within the lumen and a distal stop extending radially outward into the slot that interferes with the anchor body at the end of the slot and limits proximal movement of the plug with respect thereto. An actuation rod may be removably attached to the proximal end of the suture locking plug and project out of the proximal end of the anchor body so as to be usable to displace the locking plug within the lumen. The actuation rod may include a point of tensile weakness permitting the rod to be detached from the locking plug.

The suture pulley may be formed in a sidewall of lumen. For example, where the anchor body is tubular, the suture pulley is desirably, but not necessarily, disposed at a distal end of the tubular body. In a preferred embodiment, the lumen opens at the distal end of the tubular body and a pulley comprises a rod at the open distal end transverse to the lumen axis. The rod may rotate with respect to the anchor body, or may be fixed. Instead of a rod, the pulley may comprise a bridge formed between two spaced apertures at the distal end of the tubular body.

In another aspect of the present invention, a knotless suture anchor apparatus for anchoring a length of suture with respect thereto includes an anchor body and a suture locking plug. The anchor body has proximal and distal ends and a lumen open at the proximal end. A suture pulley fixed with expect to the anchor body permits a length of suture to be introduced into the lumen from the proximal end, looped around the pulley, and passed out of lumen through the proximal end. The suture locking plug is movable within the lumen from a first position which does not interfere with axial movement of the length of suture to a second position that compresses the length of suture against the anchor body and interferes with axial movement of the length of suture.

In accordance with a further aspect of the present invention, a knotless suture anchor apparatus for anchoring a length of suture with respect to a body cavity comprises an anchor body having an anchoring structure for fixing the anchor body within a body cavity. The anchor body has proximal and distal ends, and a lumen opening at both the proximal and distal ends, the lumen having a diameter that permits a length of suture to be passed therethrough. A suture locking plug comprises a shaft axially displaceable within the lumen from a first position which does not interfere with axial movement of the length of suture to a second position that interferes with axial movement of the length of suture. A stop is provided that positively interferes with proximal movement of the suture locking plug with respect to the anchor body.

The present invention also provides a method of securing soft tissue with respect to a body cavity without knots. The method includes passing a length of suture through soft tissue so that a loop of suture material is embedded in the soft tissue resulting in two free ends. An anchor body having an open proximal end and a lumen is provided, wherein a pulley is fixed with respect to the anchor body. The two free ends of length of suture are passed into lumen of the anchor body through the open proximal end and looped around pulley. The two free ends are extended out of lumen through the open proximal end. The anchor body is fixed with respect to a body cavity, and the loop of suture material is tightened by pulling one or both of the two free ends of the length of suture. Finally, the two free ends of the length of suture are fastened with respect to the anchor body without knots.

In the described method, the soft tissue may be a tendon and the body cavity may be formed in bone. In a particular preferred operation, the tendon is the rotator cuff tendon, and the bone is the humerus. The step of fixing the anchor body with respect to the body cavity may include forming a body cavity, passing the anchor body therein, and radially extending anchoring structure on the anchor body. In a preferred embodiment, the anchoring structure is provided on a proximal end of the anchor body and interferes with the cortical layer of the bone to prevent proximal removal of the anchor body from the cavity. The method may include providing a suture locking plug movable within the lumen from a first position which does not interfere with axial movement of the two free ends of the length of suture to a second position that compresses the two free ends of the length of suture against the lumen and interferes with axial movement thereof. The proximal actuation rod that extends out of the lumen from the proximal end of the anchor body may be coupled to the suture locking plug, wherein the method includes displacing the actuation rod in the proximal direction with respect to the anchor body, and desirably severing the actuation rod from the suture locking plug after the step of fastening.

Now, it is to be understood that the above described invention is particularly suited to locking sutures that have been passed through soft tissues and are to be anchored to bone. For example, some currently preferred methods are discussed in U.S. patent application Ser. No. 09/616,802, entitled Method & Apparatus for Attaching Connective Tissues to Bone Using a Suture Anchoring Device, filed on Jul. 14, 2000. The referenced application is commonly assigned with the present application, and is incorporated by reference in its entirety herein. Other prior art anchors, such as screws, moly bolts, and pop rivets may be adapted for use with the present invention as well.

The invention, together with additional features and advantages thereof, may best be understood by reference to the following description taken in conjunction with the accompanying illustrative drawing.

BRIEF DESCRIPTION OF THE DRAWINGS

FIG. 1A is a partial sectional view through the left shoulder of a human as seen from the front showing the use of a minimally invasive soft tissue to bone attachment system of the present invention;

FIG. 1B is an enlarged sectional view taken within the circle denoted 1B in FIG. 1A;

FIGS. 2A-2D are enlarged sectional views of the use of the soft tissue to bone attachment system of FIG. 1A to reattach a rotator cuff tendon;

FIGS. 3A-3C are partial longitudinal sectional views through a distal end of an exemplary soft tissue to bone attachment system of the present invention;

FIG. 4A is a perspective view of a combined suture locking portion and bone anchor structure of the soft tissue to bone attachment system of the present invention, showing a locking plug disengaged from an anchor body;

FIG. 4B is a partial longitudinal sectional view of the combined suture locking portion and bone anchor structure taken along line 4B-4B of FIG. 4A;

FIG. 4C is an end elevational view of the combined suture locking portion and bone anchor structure taken along line 4C-4C of FIG. 4B;

FIG. 5 is a perspective view of an anchor body of the combined suture locking portion and bone anchor structure of FIG. 6A;

FIG. 6 is a top plan view of the combined suture locking portion and bone anchor structure without the locking plug and an attached actuation rod; and FIG. 7A is a perspective view of an exemplary suture locking portion of the soft tissue to bone attachment system of the present invention showing a locking plug disengaged from an anchor body;

FIG. 7B is a partial longitudinal sectional view of the suture locking portion taken along line 7B-7B of FIG. 7A;

FIG. 7C is an end elevational view of the suture locking portion taken along line 7C-7C of FIG. 7A;

FIG. 8A is a perspective view of the exemplary suture locking portion of the soft tissue to bone attachment system of the present invention showing the locking plug engaged with the anchor body;

FIG. 8B is a partial longitudinal sectional view taken along line 8B-8B of FIG. 8A;

FIG. 8C is an end elevational view taken along line 8C-8C of FIG. 8A illustrating the locking plug clamping a length of suture against an inner lumen of the anchor body;

FIG. 10 is a partial sectional view through the left humeral head of a human as seen from the front showing the use of an alternative minimally invasive soft tissue to bone attachment system of the present invention; and FIG. 11A is a perspective view of a combined suture locking portion and bone anchor structure of the present invention, showing an alternative suture pulley structure.

FIG. 11B is a side elevational view taken along line 11B-11B of FIG. 11A, illustrating an alternative suture pulley structure.

FIGS. 17A and 17B are cross-sectional views of an embodiment illustrating a lumen wherein a plug is useable for compressing and locking the suture, and wherein the plug will not dislodge when the suture is subjected to cyclical loading.

DETAILED DESCRIPTION OF THE INVENTION

Figure 2D:
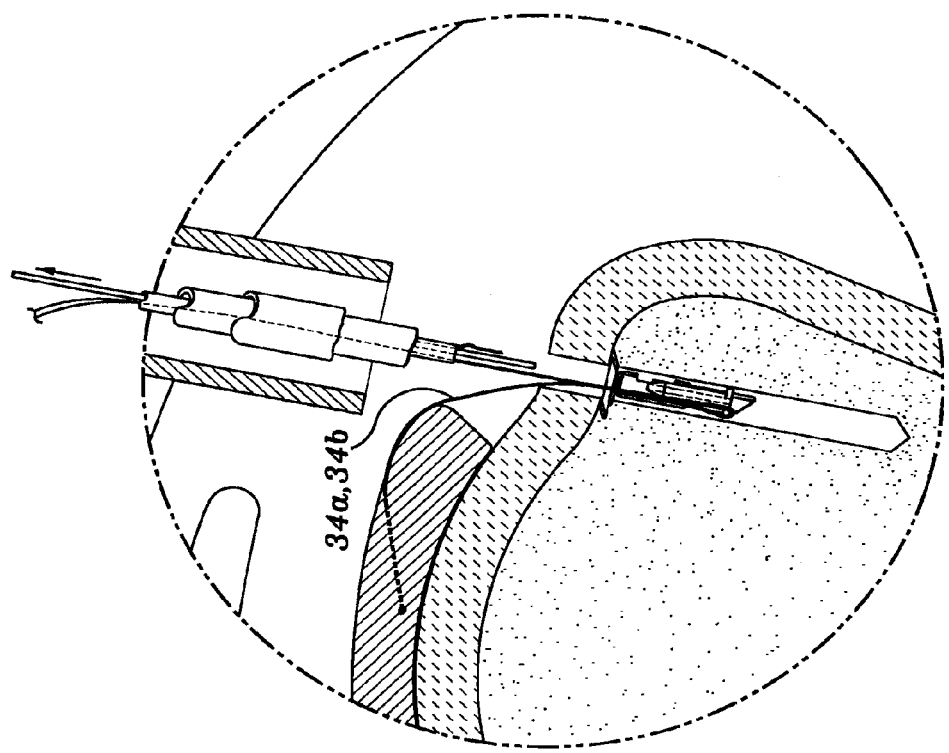

The present invention provides an improved knotless suture anchor apparatus for anchoring a length of suture with respect to a body cavity. In the exemplary embodiment described herein, the apparatus is used to anchor a length of suture to a bone structure, specifically the humeral bone of the human shoulder. The length of suture is desirably looped through soft tissue, such as a rotator cuff tendon, to approximate and fix the soft tissue with respect to the body cavity (e.g., bone structure). It should be understood, however, that the suture anchor apparatus may be utilized to secure a length of suture to body cavities other than in a bone structure, and may even be used to anchor the suture outside of a body cavity, merely to a predetermined location within the body. In this regard, the preferred apparatus includes an anchor body within which the length of suture may be anchored without knots. If the anchor body is to be implanted within the body cavity, structure on its exterior may also be provided for securing the anchor body therein. In a preferred embodiment, the anchor body is positioned within a pre-formed cylindrical cavity within a bone structure, and a bone anchor deployed from the exterior of the anchor body to hold it within the cavity.

As mentioned, the present invention is particularly well-suited for repairing rotator cuff injuries by re-attaching the rotator cuff tendon to the outside of the humeral head. The invention permits minimally invasive surgeries on such injuries and greatly facilitates rapid and secure fixation of the rotator cuff tendon to the humeral head. It should be understood that the same principles described herein apply to the repair of other injuries in which soft tissue is to be re-attached to a bone structure.

FIGS. 1A-1BA and 2A-2D are cross-sectional views through the left shoulder of a human as viewed from the front and illustrate the use of an exemplary suture anchor system 20 for repairing a rotator cuff tendon injury. The rotator cuff tendon 22 is shown in its natural positioned overlying the bulbous humeral head 24 of the humerus bone 26. In rotator cuff injuries, the tendon 22 partially or completely separates from its attachment point to the humeral head 24, which point of attachment is typically located along an angled shelf, the greater tuberosity 28. In minimally invasive surgeries to repair the rotator cuff injury, the surgeon threads one or more sutures through the rotator cuff tendon 22 and anchors them to the greater tuberosity 28. The suture anchor system 20 of the present invention facilitates this latter step of anchoring the sutures to the greater tuberosity 28.

With reference first to FIG. 1A, a generally tubular trocar 30 provides a conduit through the soft tissue of the shoulder for the suture anchor system 20 of the present invention. Typically, the surgeon makes an incision or stab wound through the outer dermal layers of sufficient size to permit passage of the trocar 30 through skin and the deltoid muscle into proximity with the humeral head 24. Various trocars and techniques for creating the approach passageway are known and may be utilized with the present invention. In addition, more than one incision and conduit may be necessary to perform the several suturing and anchoring steps.

After establishing one or more direct conduits to the humeral head 24, the surgeon passes a length of suture through the soft tissue of the rotator cuff tendon 22 so that a loop 32 of suture material is embedded therein, as seen in FIG. 1B. The two free ends 34a, 34b of the length of suture are withdrawn from the patient and coupled to the suture anchor system 20. The specifics of this coupling and subsequent manipulation of the two free ends of the suture will be described more fully below. For the purpose of explaining the exemplary method of use, it is sufficient to understand that the two free ends 34a, 34b pass into a lumen at the distal end of the suture anchor system 20 and extend through the lumen in a proximal direction to a proximal end of the system to enable fixation or pulling of the suture ends. As seen in FIG. 1B, the two free ends 34a, 34b are shown projecting from a proximal end of the system. The system 20 further includes a plurality of concentrically disposed cannulas or tubes as shown that perform the knotless suture anchoring operation. The interrelationship and functioning of these tubes will also be more fully explained below.

The exemplary system 20 as illustrated is particularly suitable for anchoring a suture to a body cavity, specifically the humeral head 24 as shown. When anchoring sutures to such a bone structure, a conventional technique is to first form a blind hole or cavity 40 through the cortical layer 42 and into the soft cancellous matter 44, as seen in FIGS. 1A-1B and 2A-2D. The surgeon then positions a suture anchor 46 within the cavity 40 and deploys it such that it cannot be removed from the cavity.

The suture anchor 46 performs two functions: anchoring itself within the body cavity and anchoring the sutures therein. In the illustrated embodiment, the former function is accomplished, e.g., using an expandable anchoring structure 48 located on the proximal end of the suture anchor 46. The anchoring structure 48 functions like a toggle bolt used in ceiling fixtures, and specifically expands to a larger dimension in the cavity 40 beyond the hard cortical bone 42. In this manner, the suture anchor 46 is prevented from being removed from the cavity 40 once the anchoring structure 48 is deployed. The present invention illustrates a particular anchoring structure 48, although any similar expedient will work. For example, a different toggle-like anchoring structure may be used such as shown in co-pending application Ser. No. 09/616,802, filed Jul. 14, 2000, the disclosure of which is hereby expressly incorporated by reference. Alternatively, an anchoring structure that expands into contact with the cancellous matter 44 may be used. In short, the present invention is not considered to be limited by the particular anchoring structure.

The second function of the suture anchor 46 is the anchoring or fixation of the suture with respect to the suture anchor itself, without the use of knots. Desirably, the particular manner of anchoring the suture with respect to the suture anchor 46 permits easy adjustment of the length of suture between the suture anchor and the loop 32 formed in the soft tissue. This adjustment allows the surgeon to establish the proper tension in the length of suture for effective repair of the soft tissue; reattachment of the rotator cuff tendon 22 in the illustrated embodiment. In this regard, FIG. 2D shows the fully deployed suture anchor 46 after the free ends 34a, 34b have been placed in tension and locked within the suture anchor. Although not shown, the remaining steps in the procedure involve withdrawing the concentric tubes from the surgical site and severing the free ends 34a, 34b close to the suture anchor 46.

Figure 3A:
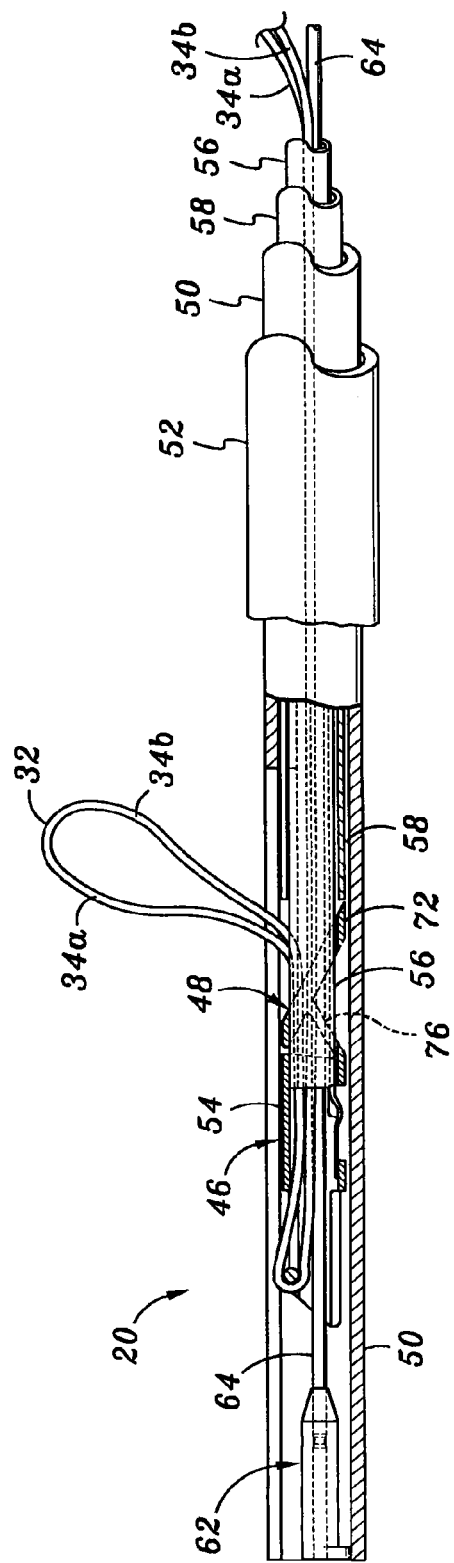

FIGS. 3A-3C are different partial longitudinal sectional views taken through the exemplary suture anchor system 20 of the present invention. The suture anchor 46 is seen in cross-section disposed in a close-fitting relationship within a delivery tube 50. The delivery tube 50, in turn, may be arranged to slide within a larger tube 52, sometimes known as an introducer tube, that includes a valve (not shown) on a proximal end to prevent fluid leakage therefrom. Alternatively, such a fluid leakage valve may be provided on the proximal end of the trocar 30 seen in FIGS. 1A-1B.

In this embodiment of the present invention, the suture anchor 46 is defined by a generally tubular anchor body 54 and an inner deployment tube 56 fits closely within a proximal end and is fastened therein. The exemplary suture anchor 46 is shown and described in greater detail below with respect to FIGS. 4-5. The deployment tube 56 can also be seen on the right side in FIG. 3A projecting from the series of concentric tubes, with the free ends 34a, 34b of the length of suture projecting therefrom. A die tube 58 sized intermediate the delivery tube 50 and the deployment tube 56 is arranged for longitudinal displacement over the deployment tube 56. In the illustrated state of the system 20, the suture anchor 46 is undeployed within the delivery tube 50 and the die tube 58 is positioned just proximal to the expandable anchoring structure 48. A further component of the suture anchor system 20 is a suture locking plug 62 having an actuation rod 64 removably attached to a proximal end thereof and extending proximally within the deployment tube 56.

FIGS. 3A-3C all show the suture loop 32 extending transversely from within the concentric tubes of the suture anchor system 20. In this regard, the delivery tube 50 is provided with an axial slot 51, the deployment tube 56 is provided with an axial slot 57, and the die tube 58 has an axial slot 59. The free ends 34a, 34b of the length of suture pass through these aligned axial slots 51, 57, 59 to the interior of the deployment tube 56 that opens into the lumen 66 of the tubular body 54. The aligned axial slots 51, 57, 59 permit passage of the free ends 34a, 34b into the system 20 from a location midway along the concentric tubes, as indicated in FIGS. 1-2.

The various described components of the suture anchor system 20 are relatively axially movable to deploy the suture anchor 46. Various means are known to relatively displace concentric tubes a predetermined distance and/or with a predetermined displacement force. For example, the concentric tubes may extend out of the trocar 30 to an actuation device in the form of concentric syringe bodies/finger tabs. Alternatively, the concentric tubes may be attached to relatively movable parts in a gun-type handle, and actuated by triggers or other such levers. It is to be understood therefore that the present invention is not limited by the particular actuation device on its proximal end, and no further description in this regard will be provided.

A more complete understanding of the exemplary suture anchor 46 will be helpful prior to a detailed description of the structure and function of the concentric tubes to deploy the system. In this regard, FIGS. 4-6 illustrate one embodiment of a suture anchor 46 isolated from the remainder of the system and having the aforementioned tubular anchor body 54 and deployable anchoring structure 48. The anchor body 54 defines a lumen 66 therewithin. FIGS. 4A and 4B also illustrate the suture locking plug 62 and attached actuation rod 64.

The anchor body 54 has the anchoring structure 48 on its proximal end and a suture pulley 70 disposed in proximity to its distal end. The aforementioned suture loop 32 is schematically illustrated out of the soft tissue for clarity, and it should be understood that this suture loop 32 is embedded in the soft tissue in actual use of the system. The free ends 34a, 34b of the length of suture pass through an angled toggle ring 72 of the anchoring structure 48 and into an open proximal end 74 of the lumen 66 formed within the tubular anchor body 54. The angled toggle ring 72 attaches to the proximal end 74 via a pair of plastically deformable struts 76. Both the toggle ring 72 and struts 76 are initially formed as a projection of the tubular anchor body 54. After continuing in the distal direction through the lumen of the anchor body 54, the free ends 34a, 34b wrap around the suture pulley 70 and traverse the lumen in the proximal direction to emerge from the angled toggle ring 72 as shown.

As best seen in FIG. 4B, the actuation rod 64 extends into an open distal mouth 76 of the anchor body 54 and through the lumen 66 and angled toggle ring 72. The actuation rod 64 and four strands of the length of suture thus share the space within the lumen 66. Because of the relatively smaller size of the actuation rod 64 with respect to the lumen 66, the length of suture may slide axially within lumen without interference. It can therefore be seen that because the suture loop 32 is embedded in soft tissue, pulling on the free ends 34, 34b of the length of suture places the suture loop in tension.

Prior to a more exhaustive description of the function of the locking plug 62 to perform the second function of the suture anchor 46 (i.e., anchoring the length of suture with respect to the suture body 54), use of the concentric tubes to deploy the anchoring structure 48 will be explained. With reference again to FIGS. 3A-3C, the deployment tube 56 can be seen attached within the lumen 66 of the anchor body 54 using a tab 80. Of course, other means for attaching the deployment tube 56 within the lumen of a body 54 may be provided, but a small tab 80 bent inwardly from the anchor body 54 and welded or otherwise secured to the deployment tube 56 is a suitable expedient. The tab 80 is desirably provided at only one location around the circumferential junction between the deployment tube 56 and lumen 66 to facilitate severing of this connection, although more than one attachment may be provided. The tab 80 thus secures the deployment tube 56 within the anchor body 54 of the suture anchor 46, while both the die tube 58 and actuation rod 64 can freely slide with respect to the anchor body 54.

After positioning the delivery tube 50 in proximity with the preformed body cavity 40 as seen in FIGS. 1A and 1B, the surgeon advances the deployment tube 56 having the suture anchor 46 attached thereto into the cavity. The suture locking plug 62 and die tube 58 advance along with the deployment tube 56, and the resulting configuration is seen in FIG. 1B.

Using a depth measurement, or visualization technique, the surgeon insures that the suture anchor 46, and in particular the anchoring structure 48, has been inserted past the hard outer layer of cortical bone 42. The anchoring structure is then expanded as seen in FIG. 2A. To accomplish this, the die tube 58 contacts the angled toggle ring 72 and forces it into an orientation that is generally perpendicular with respect to the axis of the suture anchor 46. With reference to FIGS. 3A-3C, the die tube 58 is desirably held stationary while the deployment tube 56 having the suture anchor 46 attached thereto is pulled in a proximal direction. Again, the relative movement of these tubes can be accomplished using a handle or other device exterior to the patient's body. Pulling on the deployment tube 56 forces one side of the angled toggle ring 72 against the generally circular distal mouth of the deployment tube 56 which deforms the struts 76 as the toggle ring 72 moves into a perpendicular orientation.

After the anchoring structure 48 is deployed, further pulling on the deployment tube 56 detaches it from the suture anchor 46. Specifically, the aforementioned welded tab 80 severs at a predetermined pulling force. The die tube 58 remains in place in its fixed position, and provides a reaction force against the suture anchor 46. The deployment tube 56 is then pulled free and retracted out of the way, as indicated in FIG. 2B. At this stage, the suture anchor 46 is secured with respect to the body cavity, but the length of suture passing therethrough remains free to be axially displaced.

Now with specific reference to FIGS. 3A-3C, the path of the length of suture through the suture anchor system 20 will be described. The suture loop 32 is seen projecting upward from the system, but it again should be noted that this loop is embedded in soft tissue in use of the system. The two free ends 34a, 34b extend through an axial slot 90 in the delivery tube 50, and through an axial slot 90 in the deployment tube 56 into lumen 66 of the suture can 46. As best seen in FIG. 3C, the free ends pass through the lumen 66 and around the aforementioned pulley 70. The free ends then travel in a proximal direction through the lumen 66 and through the lumen of the deployment tube 56 to emerge from proximal end of the system. Because the suture loop 32 is embedded in soft tissue, pulling on both of the free ends 34a, 34b, or pulling on one end while holding one fixed, will create tension in the length of suture. The pulley 70 provides relatively little resistance to sliding of the length of suture therearound, and thus this tensioning can be accomplished relatively easily.

In one embodiment, the pulley 70 comprises a pin oriented transversely to the axis of the suture anchor 46 and located along a sidewall thereof. As seen best in FIG. 4A, the pin may span an axial slot 100 in a sidewall of the anchor body 54 so that the free ends 34a, 34b of length of suture can pass out through the slot and around the pin. Alternatively, two axially spaced holes with chamfered or rounded edges may be formed in the sidewall of the anchor body 54 through which the free ends 34a, 34b can be threaded. Of course, numerous structures are contemplated that provide the function of the illustrated pin-type pulley 70. Moreover, instead of being a fixed structure, the pulley 70 can be arranged to swivel or otherwise move to facilitate sliding motion of the free ends 34a, 34b therearound. In a specific example, the pin-type pulley 70 can be formed separately from the anchor body 54 and inserted within a pair of facing holes in the edges of the slot 100. In this manner, the pin-type pulley 70 rotates within the holes, thus reducing friction between the free ends 34a, 34b and the pulley.

Figure 2C:
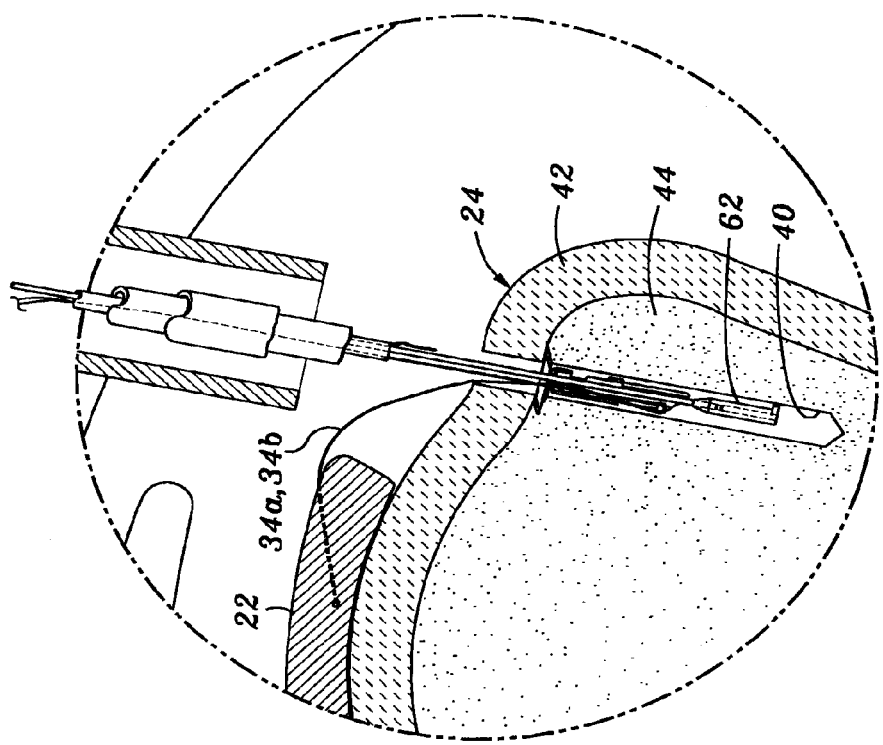

The step of tensioning the length of suture is seen in FIG. 2C, wherein the suture locking plug 62 remains in its initial position spaced from the anchor body 54. Adjustment of the length of the suture between the suture anchor 46 and the loop 32 is very important to ensure proper fixation of the rotator cuff tendon 22 with respect to the humeral head 24. If the suture is pulled too tightly, the rotator cuff tendon 22 may be unduly stressed, and the loop 32 may even pulled free from the tendon. On the other hand, if the suture is too loose, the goal of reattaching the tendon 22 in its proper location will be compromised.

Once the surgeon has established proper tension on the suture, the suture is anchored with suspect to the anchor body 54. This is done by displacing the suture locking plug 62 in a proximal direction so that it is forced into the lumen 66. The plug 62 includes a generally cylindrical shaft 102 with a bullet-shaped proximal nose 104 to help prevent its catching on the distal mouth 78 of the anchor body 54. Proximal displacement of the actuation rod 64 from outside the body causes proximal movement of the attached plug 62.

FIGS. 7-8 show the anchor body 54 without the aforementioned anchoring structure 48 for clarity. These views illustrate the movement of the suture locking plug 62 into the lumen 66, and consequent locking of the length of suture therein. The diameter of the cylindrical shaft 102 of the plug 62 is sized to be slightly smaller than the inner diameter of the lumen 66. As seen in FIGS. 8B and 8C, the diameter of the cylindrical shaft 102 is such that it compresses the four strands of the length of suture against the lumen 66. The locking plug 62 is dimensioned to compress or "crush" the length of suture in the lumen 66 and interfere with its axial movement therethrough. The amount of compression may be measured by the amount of pull force on the suture necessary to move it once the plug is in position. Desirably, the pull force is in a range that would exceed the USP (United States Pharmacopeia) Standard knot pull strength (USP 24) of the suture used. In the specific case of #2 braided polyester suture, this knot pull strength is approximately 3.5 Kgf. In practice, however, the knot pull strength of commercially available #2 braided polyester sutures approaches 14 Kgf.

Proximal displacement of the locking plug 62 within the anchor body 54 is desirably limited by a positive stop. In the illustrated embodiment, a stop flange 110 projects outwardly from the cylindrical shaft 102 at its distal end. The stop flange 110 slides within an axial slot 112 at the distal end of the anchor body 54 that terminates at a slot end 114. Although not shown in the figures, proximal movement of the locking plug 62 is ultimately restricted by contact between the stop flange 110 and the slot end 114. Of course, other configurations that provide a positive stop to proximal movement of the locking plug 62 are contemplated. For example, rather than dimensioning the locking plug 62 to be larger than the lumen 66 of the anchor body 54 (as exhibited by the stop flange 110), a stop surface may project inwardly from the lumen 66 to interfere with movement of the plug 62.

One advantage provided by the present invention is the ability to tighten a suture loop embedded within soft tissue to a predetermined tension, and then locked to the suture within a suture anchor without even slightly altering that tension. As best seen in FIG. 8B, the locking plug 62 is shown partly inserted within the tubular body 54 during the step of being pulled proximal by the actuation rod 64 as indicated by the movement arrows 116. The free ends 34a, 34b of the length of suture extend around the pulley 70, having previously been tensioned to a predetermined amount. Proximal movement of the locking plug 62 acts on all four strands of the length of suture within the lumen of the tubular body 54, and thus imparts equal frictional forces to all of the strands tending to urge them in a proximal direction. Because the four strands loop around the pulley 70, with two coming and two going, these frictional forces cancel out such that the free ends 34a, 34b do not migrate within the tubular body 54. Because the pulley 70 and tubular body 54 remain fixed with respect to the suture loop 32 (which is embedded within the soft tissue), the predetermined tension within the loop remains constant during the suture locking step.

Figure 9B:
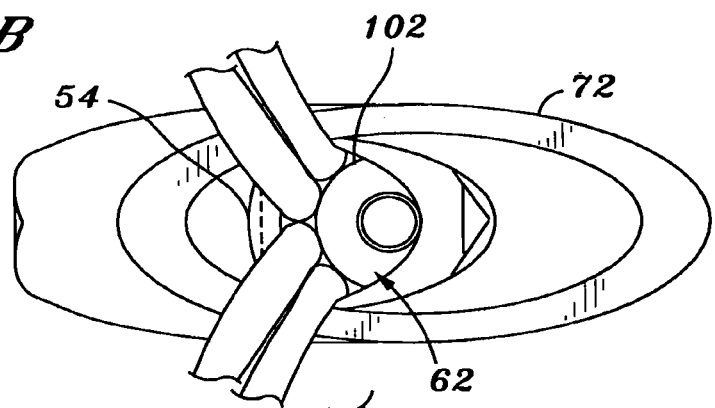
FIG. 9B is an end elevational view of FIG. 9A.
Figure 9A:
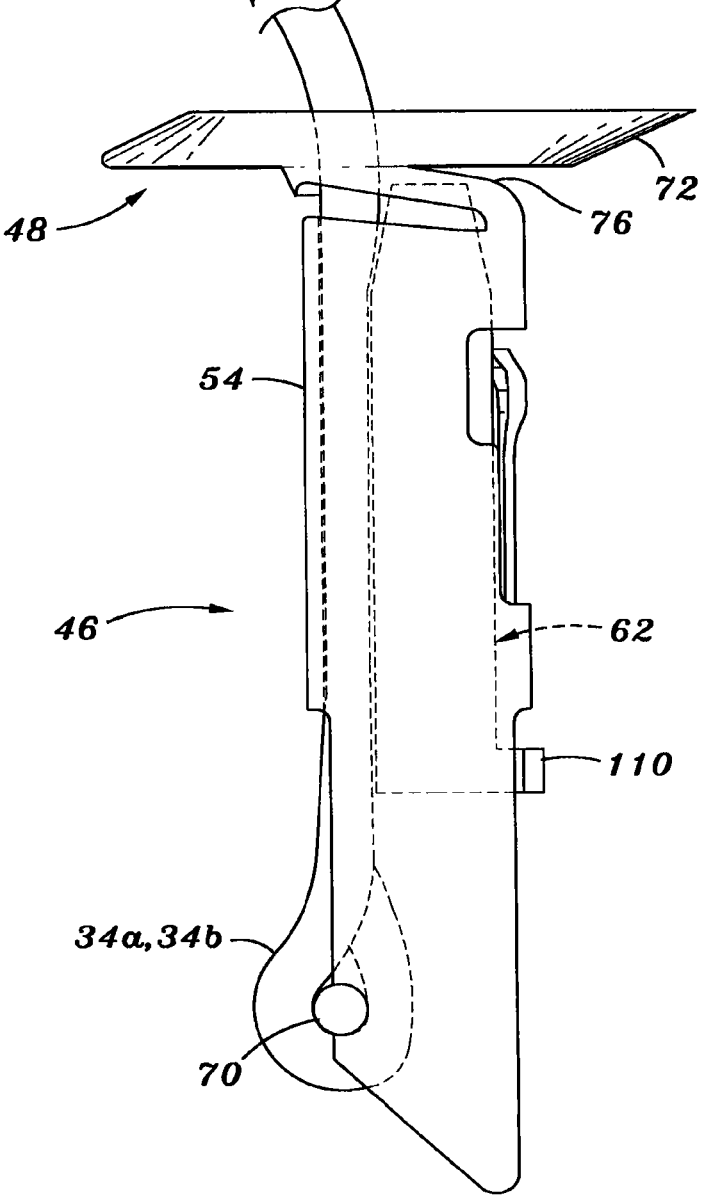
FIG. 9A is a side elevational view of the deployed anchor structure relative to the anchor body and locking plug therein.

In a further example, as seen in FIGS. 9A and 9B, deformation of the angled toggle ring 72 forces it into an oval shape at the proximal end 74 of the anchor body 54. This oval shape may have a minor dimension that is smaller than the diameter of the cylindrical shaft 102, or more typically the struts 76 may be bent into the path of the shaft 102, thus presenting an interference and a positive stop to the shaft movement. Alternatively, the actuation rod 64 may be bent back upon the exterior surface of the locking plug 62 to form the stop surface.

Once the suture locking plug 62 has been positively stopped, the actuation rod 64 may be detached therefrom. As seen in the figures, the actuation rod 64 extends within a through bore in the cylindrical shaft 102 and includes a frangible point 120 in that bore. The segment of the actuation rod distal from this frangible point 120 is secured within the bore in a conventional manner, such as with crimping indicated at 122 in FIG. 7A. The die tube 58 may be used as a reaction force against the anchor body 54 while the actuation rod 64 is pulled the proximal direction causing the frangible point 120 to sever. The final configuration is seen in FIG. 2D.

As mentioned above, the exemplary structure for locking sutures relative to a body cavity may be utilized in a variety of anatomical environments. For instance, FIG. 10 shows an alternative surgical technique for using a combined suture anchor 46' and anchoring structure 48' to repair a rotator cuff tendon 22. In this embodiment, rather than forming a blind cavity within the humeral head 24, the surgeon forms a cavity 130 that transects the greater tuberosity 28 and opens through the cortical layer 42 at both ends. After embedding the loop 32 of suture material within the rotator cuff tendon 22, the free ends 34a, 34b are inserted into and threaded through the cavity 130. The ends 34a, 34b are then passed through the lumen formed within the combined suture anchor 46' and anchoring structure 48', which combination is then inserted as shown into the cavity 130. The free ends 34a, 34b of suture are then tightened to the prescribed level and secured within the suture anchor 46'. It should be noted that the combined suture anchor 46' and anchoring structure 48' may be configured somewhat differently to permit the aforementioned tightening step, though the suture locking steps are preferably accomplished in the same manner as described above; namely, with a suture locking plug compressing the length of suture within the suture anchor 46'. Furthermore, the anchoring structure 48' contacts the exterior of the cortical bone rather than the interior as described above.

FIG. 11 illustrates an alternative suture anchor 140 of the present invention having a body cavity anchoring structure 142 on a proximal end. A length of suture is shown having a loop 144 and a pair of free ends 146a, 146b passing through the anchoring structure 142 and through a lumen 148 of a generally tubular body 150 of the suture anchor 140. In a distal portion of the tubular body 150, the free ends 146a, 146b pass out of the lumen 148 through a first aperture 152a and re-enter the lumen through a second aperture 152b located distally from the first aperture. As illustrated, the lumen 148 in the region of the apertures 152a, 152b is only partly defined by a semi-cylindrical extension of the tubular body 150, but other arrangements having a more complete lumen at this location are within the scope of the present invention.

With reference to FIG. 11B, the apertures 152a, 152b are shown to be rounded to reduce abrasion on the suture free ends 146*a*, 146*b*. In addition, the bridge portion 154 of the tubular body 150 that separates the apertures 152*a*, 152*b* defines a pulley structure, much like the pulley 70 (FIG. 8B) described above in the earlier embodiment. That is, the suture free ends 146*a*, 146*b* can easily slide with respect to the bridge portion 154, especially because of the rounded corners, to permit tightening of the suture loop 144 prior to locking the length of suture within the tubular body 150. The length of suture may be locked within the tubular body 150 using a locking plug as described above, or with another similar expedient.

FIGS. 12-16 illustrate another suture locking anchor in accordance with the present invention. Similar to the above embodiments, bone anchor 200 includes an anchor body 210, an anchoring or embedding structure 280, a suture return member 230 (such as, but not limited to, a pulley or pin), and a suture locking plug 240.

Similar to the embodiments described above, suture locking plug 240 is actuated or deployed to compress suture 250 against the anchor body 210. In one embodiment, the plug 240 has a smaller outer diameter than the inner diameter of the lumen of the anchor body 210. The gap between the members may range from about 0 to 0.025 inches and more preferably from about 0.011 to 0.013 inches. As such, the suture is locked due to compression.

Figure 14:
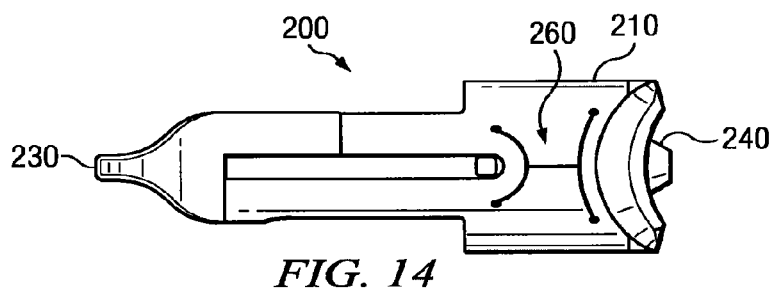
FIG. 14 is a top view of the anchor shown in FIG. 12 in a deployed configuration.
Figure 15:
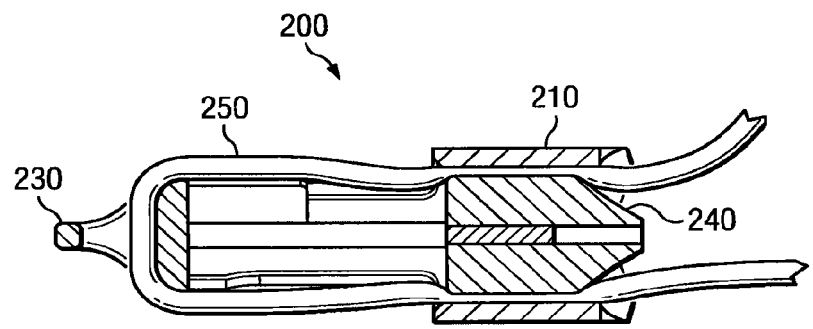
FIG. 15 is a cross section of the anchor shown in FIG. 14 illustrating a suture locked in place between the anchor body and the plug member.

FIG. 14 illustrates an anchor body having a deformable section 260. The deformable section 260 shown in FIG. 14 comprises slits and openings in the lumen of the anchor body. This deformable region serves to accommodate and secure sutures of different diameters. An advantage of deformable region or section 260 is that a relatively large suture or a small suture may be compressed between plug 240 and anchor body 210 to firmly lock the suture in place without damaging the suture. For example, a #2 suture or #5 suture may be locked in place using the same anchor 200 of the present invention. Regardless of the size of the suture, the cooperation between the plug, lumen, and deformable section secures and prevents axial movement of the suture.

A wide variety of deformable sections may be incorporated into the anchor body 210 to accommodate and secure the suture. For example, the deformable section may have a thin wall relative to other areas of the anchor body. The deformable section may be made of less rigid material than other areas of the anchor body. The deformable anchor may comprise slits, springs, zigzag members, ribs, and other geometries to accommodate and secure a wide variety of suture sizes and types. Also, depending on the deformation design, plastic or elastic deformation may occur. Indeed, resilient, or flexible materials and designs may be incorporated into the present invention.

Likewise, the plug member may incorporate a deformable section to accommodate the suture size range. Additionally, one or both structures may incorporate a deformable section to accommodate and secure the suture.

An exemplary material for the anchor body is stainless steel. However, a wide variety of materials may be suitable. The anchor body may be made of a number of types of metals and plastic including but not limited to stainless steel, titanium, peek, polycarbonate, polysulfone, polyester, polyethylene, bio-absorbable plastics, bio-active materials, and combinations thereof.

In another embodiment of the present invention, the plug and anchor body are made of different materials such that at least one of the components deforms under pressure of the other component. For example, the anchor wall may be made of a less rigid material than the plug or vice versa.

Additionally, the plug and anchor body may be made of a rigid material and an intermediate, deformable material, or flexible material may be associated with, or applied to either component to supply an interface which will flex or deform to accommodate sutures of different diameters. If applied to a metal anchor body, this intermediate deformable (or flexible) member may be, e.g., a polymer tube that is attached to the ID of the anchor body. If applied to a metal plug, this intermediate deformable (or flexible) member may be, e.g., a polymer sleeve or coating that is attached to the OD of the plug. This intermediate component may also have a similar hardness to that of the suture. The intermediate component serves to allow conformity and flexibility within the locking structure to accommodate different suture sizes. Also, instead of providing an intermediate conforming component, a spring mechanism may be inserted into either the rigid plug or anchor body that allows the pertinent rigid surfaces to flex and accommodate various suture diameters.

Figure 12:
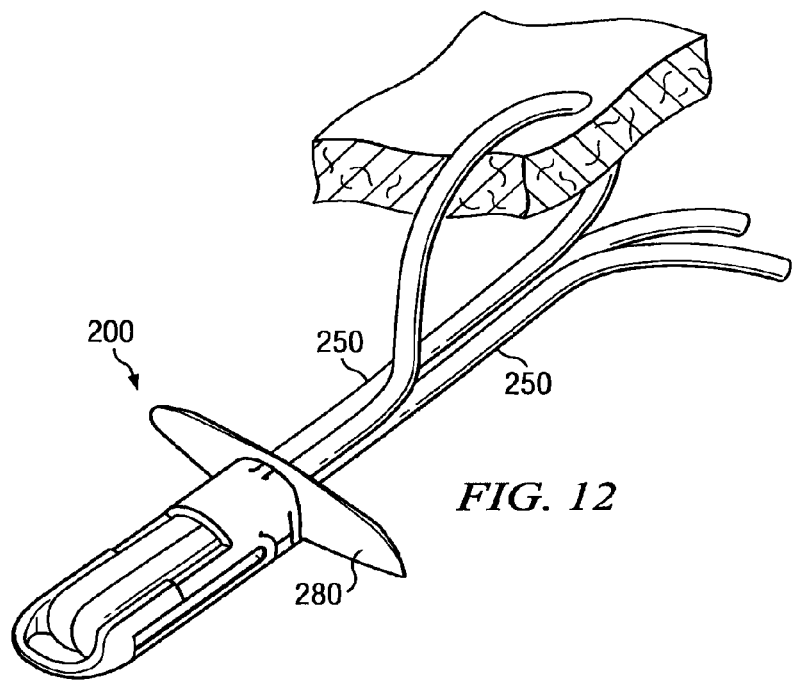
FIG. 12 is a perspective view of a combined suture locking portion and bone anchor structure of the present invention, showing an alternative bone locking and suture locking structure.
Figure 13:
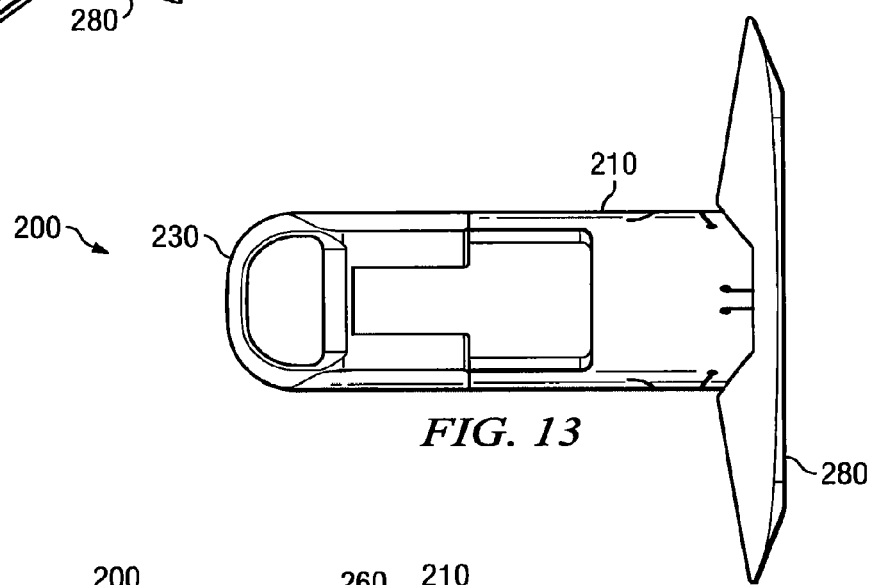
FIG. 13 is a side view of the anchor shown in FIG. 12 in a deployed configuration.

FIGS. 12-13 illustrate another anchoring structure 280. In particular, anchoring structure 280 may comprise a first member and second member that is urged into a position transverse to the longitudinal axis of the bone anchor. As such, the bone anchor assumes a larger profile and becomes locked in the wall of the bone passage (not shown). Various bone anchoring structures may be utilized with the anchors of the present invention. Indeed, any of the features described in the various embodiments and figures may be combined with different features described herein and are to be considered part of the present invention. Additionally, other anchoring structures include barbs, threads, expansion ribs, molybolts, rivets, and other mechanisms may be utilized to affix the anchor in the bone passage.

Figure 16:
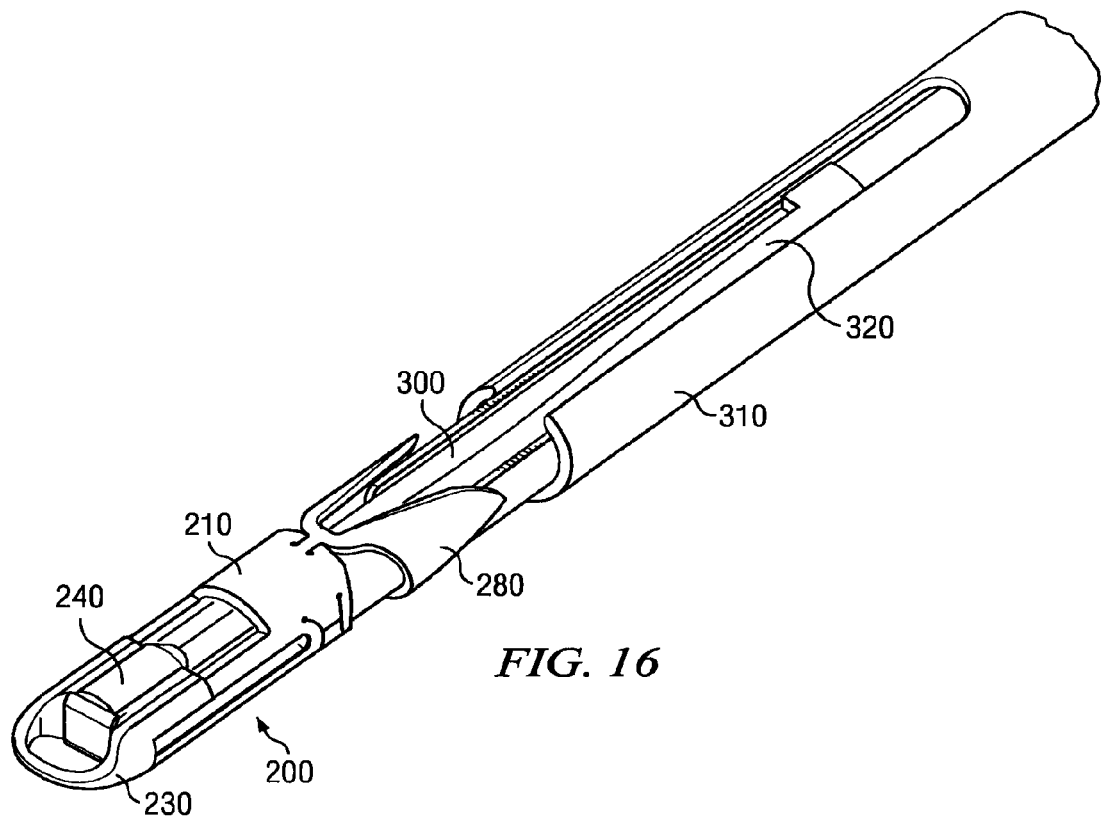
FIG. 16 is partial perspective view of an anchor and plug in accordance with one embodiment of the present invention, detachably coupled to an insertion instrument.

The anchoring structure 280 may be deployed or activated by an instrument as shown in FIG. 16. The instrument includes a shaft, die 310 that moves relative to the anchoring structure so as to urge the first and second members radially outwards.

After the anchor has been actuated to affix it in a bone passage, one or both ends of the suture are tensioned to approximate the tissue to the bone. That is, the tissue is moved into a desired location. An instrument to facilitate this tissue approximation and method is described in U.S. Pat. No. 6,780,198.

The instrument is actuated again to move suture locking plug 240 into a second locked position, thereby compressing a suture between the anchor body and the plug. The instrument is actuated again to detach the suture plug from the instrument. In the embodiment shown in FIG. 16, a ribbon member detachably connects the plug with the instrument.

It is also to be appreciated that the above described bone anchor incorporating a deformable section may be adjusted to provide a predetermined spring load on a suture in the suture lock thus controlling the attachment characteristics of the suture-tissue construct to the anchor. Obtaining a predetermined spring load may be accomplished by varying spring constants and preloads through the choice of materials, spring geometries, and spring configurations. Such design considerations may expand beyond the range of common spring design to include the design of deformable section in the material's plastically deforming body or envelope.

Figures 18A, 18B:
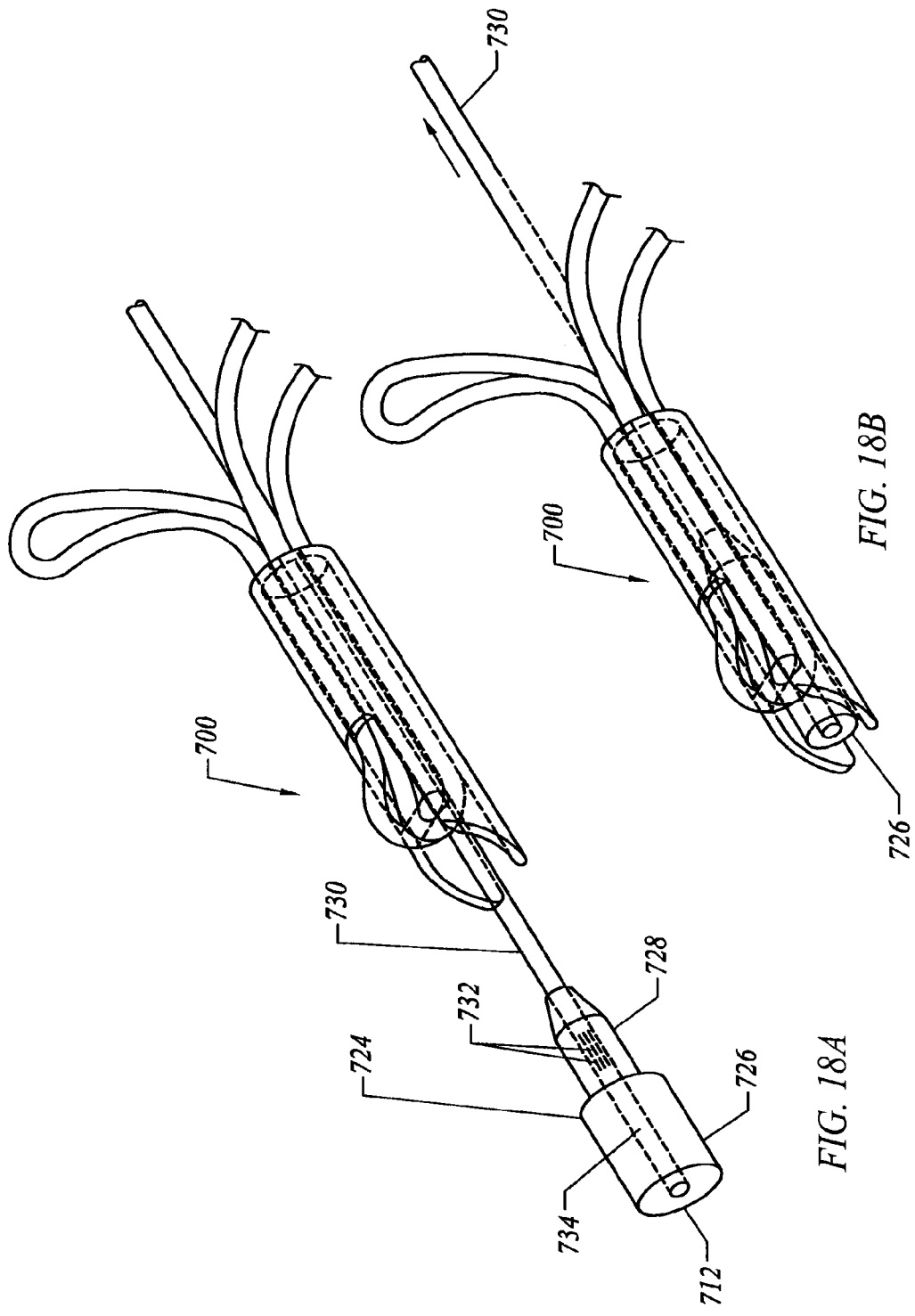
FIGS. 18A and 18B are perspective views of the plug located in the lumen at first and second positions in the lumen.
Figure 19:
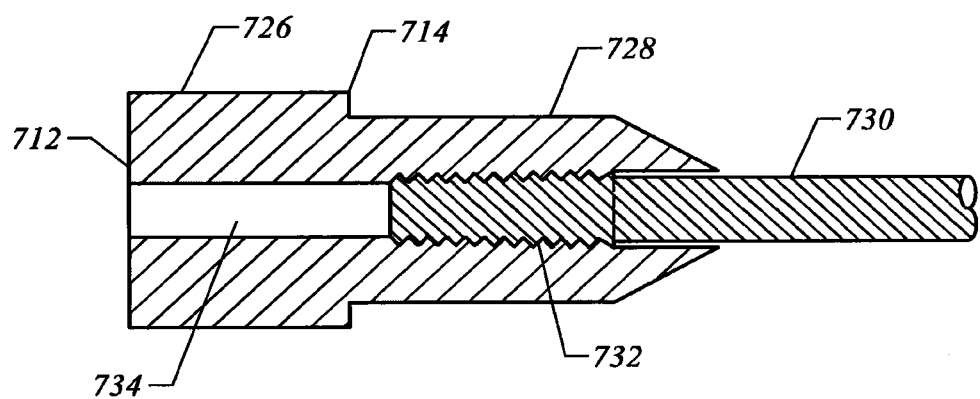
FIG. 19 is a cross-section view of an embodiment of the plug member.
Figure 20:
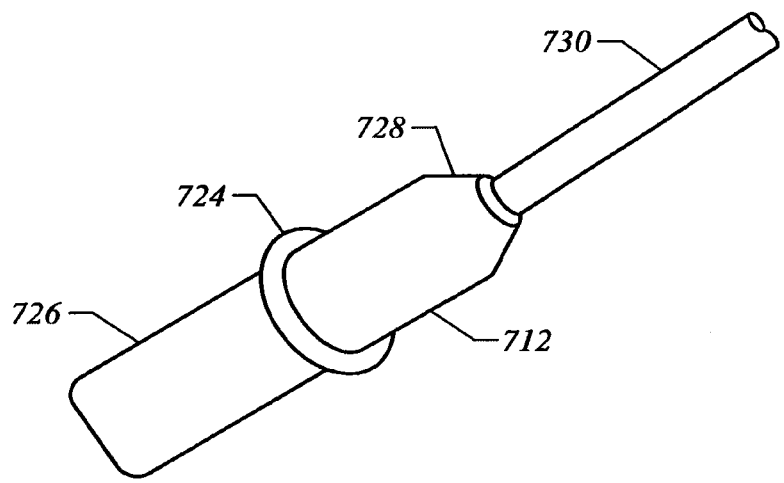
FIG. 20 is a perspective view of an embodiment of the plug member.

In another embodiment illustrated in FIGS. 17-20, a suture-locking apparatus (700) comprises a body member (702) having a proximal end (704), a distal end (706), and an axial lumen (708) formed in between the proximal and distal ends. In one embodiment, the proximal end is adapted for passing a portion of a suture (710) into the lumen. The apparatus in this embodiment includes a plug member (712) that can be moved from a first position as illustrated in FIG. 17A where the plug member does not interfere with movement of the suture in the lumen, to a second position as illustrated in FIG. 17B where the plug member interferes with movement of the suture in the lumen by compressing it against the wall of the lumen. In this embodiment, the plug member is provided with a radial protrusion (714, 724) adapted for compressing and thus locking the suture in the lumen at the second position. In one embodiment, the radial protrusion is in the form of a circumferential step feature (714) on the plug member as illustrated in FIG. 19; in another embodiment the radial protrusion is a circumferential stop ridge (724) formed on the plug member as illustrated in FIG. 20. In alternative embodiments not shown, the location and or shape of the protrusion on the plug can be varied within the scope of the invention to compress the suture and restrict the length of travel of the plug in the lumen.

The radial protrusion of the plug in its various embodiments preferably performs one or more functions including, for example, stopping the axial movement of the plug within the lumen in the proximal direction; and compressing and locking the suture against the wall in the lumen, thereby securing the suture in the lumen without the need to tie the suture with a knot.

The radial protrusion (in cooperation with a matching feature in the wall of the lumen as illustrated in FIGS. 17A and 17B) safeguards against pulling the plug out of the lumen as the suture is placed under tension. Thus in one embodiment as shown in FIGS. 17A and 17B, the lumen is characterized by a larger internal wall cross-section (718) within a first position, and a smaller internal wall cross-section at the second position (720), the larger cross-section transitioning to the smaller cross-section at a zigzag wall section (722) therein. In this embodiment the zigzag path in the wall of the lumen cooperates with the radial protrusion on the plug to compress the suture and stop the plug from axially advancing in the proximal direction.

In compressing and locking the suture against the wall in the lumen as illustrated in FIGS. 17A and 17B, the radial protrusion in this embodiment establishes a zigzag path and thus a zigzag interface between the plug and the lumen wall such that the surfaces are parallel and perpendicular to the direction of tension on the suture. This configuration of the interface and the suture therein provides for a significant increase in the frictional force and thus an increased locking efficiency on the suture.

In one embodiment the plug as illustrated in FIGS. 17-20 is shaped in the form of a bullet with a nose (728) and tail (726) sections that are sized slightly smaller than the inner diameter of the lumen (708). As is illustrated for example in FIG. 17B, at the second position, the diameter of the distal section of the tail is such that the plug can be urged against the zigzag portion of the lumen wall to compresses the suture while simultaneously interfering with the axial movement of the plug in the proximal direction. The amount of compression may be measured by the amount of tension on the suture necessary to move it once the plug is in position. Desirably, the tension is in a range that would exceed the USP (United States Pharmacopeia) Standard knot pull strength (USP 24) of the suture used. In the specific case of #2 braided polyester suture, this knot pull strength is approximately 3.5 Kgf. In practice, however, the knot pull strength of commercially available #2 braided polyester sutures approaches 14 Kgf.

In one embodiment the plug is provided with an actuation member (730) for use in inserting the plug into the lumen and for axially moving the plug in the lumen from the first position to the second position as illustrated in FIGS. 17A, 17B, 18A and 18B. Another feature provided on the present embodiment is an aperture (716) through the body portion that opens into the lumen at the distal end plug.

In one embodiment a suture pulley member (716) fixed with respect to the lumen is provided for reversing the path of the suture in the lumen at the distal end such that the suture can exit the lumen at the proximal end. In an embodiment wherein the body member is in the form of a tubular body as illustrated in FIG. 17B, the suture pulley member comprises a portion of the tubular body defined between the aperture and the distal end. In another embodiment the pulley member comprises a rod member. In another embodiment the suture pulley member comprises a bridge member defined between two apertures in said body member. In the various embodiments the pulley member is deployed transversely across said lumen as illustrated in FIGS. 18A and 18B.

In another embodiment as illustrated for example in FIGS. 17A and 17B the suture-locking apparatus comprises a toggle member (736) disposed proximally and axially with the body member (702). Connecting the toggle member to the body member is at least one strut member (738). In an undeployed position the toggle member projects a smaller profile transverse to the body member, and at a deployed position projects a larger profile transverse to the body member. In one embodiment the strut member is adapted so as to collapse and translate the toggle member from the undeployed position to the deployed position.

In various embodiments the components of the present suture lock can be made from a material suitable for implant in the body. Examples of such materials include plastics, a polyaryletheketone and stainless steel.

In a further embodiment the present suture anchor can be used to anchor soft tissue in a body cavity using a suture without tying a knot, in a method that includes the steps of: (i) suturing the soft tissue such that at least one free end of the suture is available; (ii) passing the free end of the suture into the lumen through the open proximal end, looping the free end around the pulley, and extending the free end out of the lumen through the open proximal end; (iii) embedding the suture-anchor with respect to a body cavity; (iv) tensioning the suture by pulling on the free end; and (v) compressing the suture against a radial protrusion on a movable suture-locking plug member within the lumen, thereby securing the suture without tying a knot on the suture.

In this procedure, the soft tissue may be a tendon and the body cavity may be formed in bone. In a particular preferred procedure, the tendon is the rotator cuff tendon, and the bone is the humerus. The step of fixing the anchor body with respect to the body cavity may include forming a body cavity, passing the anchor body therein, and radially extending anchoring structure on the anchor body. In a preferred embodiment, the anchoring structure is provided on a proximal end of the anchor body and interferes with the cortical layer of the bone to prevent proximal removal of the anchor body from the cavity. The method may include providing a suture-locking plug movable within the lumen from a first position which does not interfere with axial movement of the two free ends of the length of suture to a second position that compresses the two free ends of the length of suture against the lumen and interferes with axial movement. The proximal actuation rod that extends out of the lumen from the proximal end of the anchor body may be coupled to the suture-locking plug, wherein the method includes displacing the actuation rod in the proximal direction with respect to the anchor body, and desirably severing the actuation rod from the suture-locking plug after the step of fastening.

Accordingly, although an exemplary embodiment of the invention has been shown and described, it is to be understood that all the terms used herein are descriptive rather than limiting, and that many changes, modifications, and substitutions may be made without departing from the spirit and scope of the invention. In particular, it is noted that the procedures, while oriented toward the arthroscopic repair of the rotator cuff, are applicable to the repair of any body location wherein it is desired to attach or reattach soft tissue to bone, particularly using an arthroscopic procedure.

All patents and patent applications mentioned above, including U.S. patent application Ser. Nos. 09/781,793; 11/143,132; and 60/799,116, are incorporated by reference in their entirety.

What is claimed is:

1. A knotless suture anchor apparatus for anchoring a length of suture with respect thereto, comprising:
   an anchor body comprising a lumen, the lumen sized to freely accommodate the length of suture disposed within the lumen;
   wherein the anchor body comprises a rigid section and a deformable section; and
   a suture locking plug movable within the lumen, wherein the suture locking plug compresses the length of suture against the anchor body within the deformable section, the deformable section sized to deform only by the presence of both the length of suture and the suture locking plug such that the length of suture is selectively secured as the length of suture is compressed.

2. The apparatus of claim 1, wherein the suture locking plug is movable within the lumen of the anchor body from a first position which does not interfere with an axial movement of the length of suture to a second position that interferes with the axial movement of the length of suture as the length of suture is compressed.

3. The apparatus of claim 1, wherein the anchor body is generally tubular and the lumen opens at a distal end as well as at a proximal end.

4. The apparatus of claim 3, further comprising a suture return path such that the length of suture may be introduced into the lumen from the proximal end and passed out of the lumen through the proximal end.

5. The apparatus of claim 1 wherein said deformable section comprises at least one slit or opening.

6. The apparatus of claim 1 wherein the deformable section flexes outwardly in response to the pressure from the suture locking plug.

7. The apparatus of claim 1 wherein the deformable section is expandable to accommodate at least two of the length of suture, each of the at least two length of suture having varying diameters.

8. The apparatus of claim 4, wherein a suture return member is deployed transversely across the lumen and within the suture return path.

9. The apparatus of claim 8, wherein the suture return member is a pin.

10. The apparatus of claim 1, further comprising an anchoring structure for fixing the anchor body within a body cavity.

11. The apparatus of claim 10, wherein said anchor structure comprises a first deflecting member and a second deflecting member attached to the proximal end of the body member, and wherein each of the first deflecting member and the second deflecting member comprises a low profile undeployed position and a larger profile deployed position.

12. The apparatus of claim 10, wherein the anchoring structure comprises:
   a toggle member disposed proximally to and axially with said anchor body; and
   a strut member connecting said toggle member to said anchor body,
   wherein said toggle member when disposed at an undeployed position projects a smaller profile transverse to said anchor body, and at a deployed position projects a larger profile transverse to said anchor body, said strut member adapted for collapsing to translate said toggle member from said undeployed position to said deployed position.

13. The apparatus of claim 1 wherein said deformable section comprises a wall thickness less than that of another portion of said lumen.

14. The apparatus of claim 1, wherein said deforming section is adapted to provide elastic deformation.

15. The apparatus of claim 1, wherein said deforming section is adapted to provide plastic or inelastic deformation.

16. The apparatus of claim 2, wherein said length of suture is movable in said lumen while said suture locking plug is located at said first position.

17. The apparatus of claim 2, wherein said suture locking plug is movable from said first position to said second position while said length of suture is attached to a body tissue.

18. A kit comprising:
   a first suture having a first diameter;
   a second suture having a second diameter different than said first diameter; and
   a knotless suture anchor apparatus as recited in any one of the above claims to accommodate both of said first suture or said second suture and prevent said suture from axial movement when said suture locking plug is in said second position.

19. The kit of claim 18 further comprising an insertion instrument to deploy said apparatus and tension at least one of said first and second suture.

20. The kit of claim 19 wherein the insertion instrument allows for separate actuation of the anchoring structure and the suture locking plug.

* * * * *